(12) United States Patent
Knott et al.

(10) Patent No.: US 9,481,695 B2
(45) Date of Patent: Nov. 1, 2016

(54) AMINO ACID-MODIFIED SILOXANES, PROCESS FOR PREPARING THEM AND APPLICATION

(71) Applicant: Evonik Industries AG, Essen (DE)

(72) Inventors: Wilfried Knott, Essen (DE); Frauke Henning, Essen (DE); Sadik Amajjahe, Duesseldorf (DE); Sarah Krauskopf, Bochum (DE); Michael Fiedel, Essen (DE); Olga Jazkewitsch, Essen (DE); Christian Hartung, Essen (DE)

(73) Assignee: EVONIK INDUSTRIES AG, Essen (DE)

( * ) Notice: Subject to any disclaimer, the term of this patent is extended or adjusted under 35 U.S.C. 154(b) by 197 days.

(21) Appl. No.: 14/331,831

(22) Filed: Jul. 15, 2014

(65) Prior Publication Data

US 2015/0023900 A1 Jan. 22, 2015

(30) Foreign Application Priority Data

Jul. 18, 2013 (DE) ........................ 10 2013 214 081

(51) Int. Cl.
| | |
|---|---|
| C07F 7/18 | (2006.01) |
| C07F 9/54 | (2006.01) |
| C07C 279/14 | (2006.01) |
| C07C 229/24 | (2006.01) |
| C08G 77/388 | (2006.01) |
| A61Q 5/12 | (2006.01) |
| C07C 229/26 | (2006.01) |
| C07C 211/63 | (2006.01) |
| C11D 3/00 | (2006.01) |
| A61K 8/58 | (2006.01) |

(52) U.S. Cl.
CPC ............ C07F 7/1804 (2013.01); A61K 8/585 (2013.01); A61Q 5/12 (2013.01); C07C 211/63 (2013.01); C07C 229/24 (2013.01); C07C 229/26 (2013.01); C07C 279/14 (2013.01); C07F 9/5407 (2013.01); C08G 77/388 (2013.01); C11D 3/001 (2013.01); *A61K 2800/10* (2013.01)

(58) Field of Classification Search
CPC .. C07F 7/1804; C07F 9/5407; C07C 279/14; C07C 229/24; C07C 229/26; C07C 211/63; C08G 77/388; A61Q 5/12; C11D 3/001; A61K 8/585; A61K 2800/10
See application file for complete search history.

(56) References Cited

U.S. PATENT DOCUMENTS

| | | | |
|---|---|---|---|
| 5,371,161 A | 12/1994 | Knott | |
| 5,412,074 A | 5/1995 | Jones et al. | |
| 5,430,166 A | 7/1995 | Klein et al. | |
| 5,430,167 A | 7/1995 | Klein et al. | |
| 5,455,367 A | 10/1995 | Klein et al. | |
| 5,475,127 A | 12/1995 | Klein et al. | |
| 5,516,869 A | 5/1996 | Lucarelli et al. | |
| 5,606,077 A | 2/1997 | Lersch et al. | |
| 6,255,511 B1 | 7/2001 | Klein et al. | |
| 6,489,498 B2 | 12/2002 | Klein et al. | |
| 6,858,663 B2 | 2/2005 | Knott et al. | |
| 7,018,458 B2 | 3/2006 | Knott et al. | |
| 7,125,585 B2 | 10/2006 | Dudzik et al. | |
| 7,157,541 B2 | 1/2007 | Knott et al. | |
| 7,196,153 B2 | 3/2007 | Burkhart et al. | |
| 7,598,334 B2 | 10/2009 | Ferenz et al. | |
| 7,612,158 B2 | 11/2009 | Burkhart et al. | |
| 7,612,159 B2 | 11/2009 | Burkhart et al. | |
| 7,635,581 B2 | 12/2009 | Ferenz et al. | |
| 7,645,848 B2 | 1/2010 | Knott et al. | |
| 7,754,778 B2 | 7/2010 | Knott et al. | |
| 7,825,205 B2 | 11/2010 | Knott et al. | |
| 7,825,206 B2 | 11/2010 | Neumann et al. | |
| 7,825,209 B2 | 11/2010 | Knott et al. | |
| 7,855,265 B2 | 12/2010 | Thum et al. | |
| 8,138,294 B2 | 3/2012 | Henning et al. | |
| 8,198,473 B2 | 6/2012 | Ferenz et al. | |
| 8,211,972 B2 | 7/2012 | Meyer et al. | |
| 8,247,525 B2 | 8/2012 | Schubert et al. | |
| 8,268,939 B2 | 9/2012 | Ebbrecht et al. | |
| 8,283,422 B2 | 10/2012 | Schubert et al. | |
| 8,309,664 B2 | 11/2012 | Knott et al. | |
| 8,309,673 B2 | 11/2012 | Schubert et al. | |
| 8,334,355 B2 | 12/2012 | Henning et al. | |
| 8,420,748 B2 | 4/2013 | Henning et al. | |
| 8,455,603 B2 | 6/2013 | Ferenz et al. | |
| 8,466,248 B2 | 6/2013 | Meyer et al. | |
| 8,557,944 B2 | 10/2013 | Henning et al. | |
| 8,598,295 B2 | 12/2013 | Henning et al. | |

(Continued)

FOREIGN PATENT DOCUMENTS

| | | |
|---|---|---|
| DE | 10327871 | 1/2005 |
| EP | 1149855 A1 | 10/2001 |

(Continued)

OTHER PUBLICATIONS

Wang, Y., et al., "The self-organization properties of n-dodecylammonium [alpha]-glutamate/n-C5H11OH/water system", Colloid and Polymer Science; Jul. 2007, pp. 1423-1431, 285, Springer, Berlin, DE.

(Continued)

*Primary Examiner* — Trevor Love
(74) *Attorney, Agent, or Firm* — Scully, Scott, Murphy & Presser, P.C.

(57) ABSTRACT

A process for preparing amino acid-modified siloxanes that can be carried out under mild conditions is provided as well as organically modified silicones for care formulations for skin, hair and textiles that are toxicologically unobjectionable.

4 Claims, No Drawings

(56) References Cited

U.S. PATENT DOCUMENTS

| | | |
|---|---|---|
| 8,609,798 B2 | 12/2013 | Knott et al. |
| 8,623,984 B2 | 1/2014 | Henning et al. |
| 8,685,376 B2 | 4/2014 | Czech et al. |
| 8,722,834 B2 | 5/2014 | Knott et al. |
| 8,722,836 B2 | 5/2014 | Knott et al. |
| 8,729,207 B2 | 5/2014 | Hartung et al. |
| 2007/0128143 A1 | 6/2007 | Gruning et al. |
| 2010/0029587 A1 | 2/2010 | Bruckner et al. |
| 2010/0081781 A1 | 4/2010 | Schubert et al. |
| 2011/0021693 A1 | 1/2011 | Henning et al. |
| 2011/0230619 A1 | 9/2011 | Kuppert et al. |
| 2011/0251070 A1 | 10/2011 | Poffenberger et al. |
| 2011/0301254 A1 | 12/2011 | Knott et al. |
| 2012/0190760 A1 | 7/2012 | Henning et al. |
| 2012/0190762 A1 | 7/2012 | Hubel et al. |
| 2012/0282210 A1 | 11/2012 | Henning et al. |
| 2012/0294819 A1 | 11/2012 | Herrwerth et al. |
| 2012/0308494 A1 | 12/2012 | Schubert et al. |
| 2013/0035408 A1 | 2/2013 | Knott et al. |
| 2013/0040875 A1 | 2/2013 | Henning et al. |
| 2013/0041115 A1 | 2/2013 | Knott et al. |
| 2013/0174760 A1 | 7/2013 | Henning et al. |
| 2013/0213267 A1 | 8/2013 | Fiedel et al. |
| 2013/0217907 A1 | 8/2013 | Henning et al. |
| 2013/0217930 A1 | 8/2013 | Haensel et al. |
| 2013/0259821 A1 | 10/2013 | Henning et al. |
| 2013/0331592 A1 | 12/2013 | Hartung et al. |
| 2013/0345318 A1 | 12/2013 | Schubert et al. |
| 2014/0094532 A1 | 4/2014 | Knott et al. |
| 2014/0134125 A1 | 5/2014 | Dahl et al. |

FOREIGN PATENT DOCUMENTS

| | | |
|---|---|---|
| EP | 1477512 A1 | 11/2004 |
| JP | 2004182680 | 7/2004 |
| WO | WO2009084711 A1 | 7/2009 |

OTHER PUBLICATIONS

Rodehueser, L., et al., "Derivatives of glutamic acid as new surfactants", Amino Acids, Jan. 2000, 18, pp. 89-100, Springer Verlag, AU.

Gardas, R. L., et al., "Thermophysical Properties o f Amino Acid-Based Ionic Liquids", Journal of Chemical & Engineering Data, Apr. 2010, 55, pp. 1505-1515.

European Search Report dated Sep. 2, 2014 received in a corresponding foreign application.

AMINO ACID-MODIFIED SILOXANES, PROCESS FOR PREPARING THEM AND APPLICATION

FIELD OF THE INVENTION

The present invention relates to amino acid-modified siloxanes, to their preparation processes and to their application in care formulations for skin, hair and textiles.

BACKGROUND

Siloxanes comprising nitrogen functionality, more particularly siloxanes carrying amino groups, are claiming increased importance in the textile finishing sector, and also for important leave-on applications in the cosmetics additives sector, such as, for example, hair conditioning. Not least from the standpoint of sustainability, but also that of biomimetics, those systems that are of interest in this context are the systems which derive from natural starting materials such as amino acids, proteins and their derivatives.

The chemical linking of the siloxane structures and amino acid or protein structures, which are diametrically different as compounds, always poses a synthetic challenge. The task is therefore to overcome the difficulties presented by the differences in solubility behavior between siloxanes and amino acids. There has therefore been no lack of multifarious efforts to gain access to these interesting classes of substance, utilizing any of a very wide variety of chemical linking approaches.

For example, EP 1149855 describes one possible method for preparing arginine-functionalized siloxanes, using anhydride-functionalized siloxanes. The anhydride functionality is introduced, for example, by hydrosilylation of allylsuccinic anhydride, which is expensive and toxicologically objectionable. The siloxane is subsequently reacted with an excess of unprotected arginine in ethanol.

JP 2004-182680 describes a cosmetic product which comprises a silicone polymer modified by an amino acid derivative. In this case, a complex 4-stage synthesis is deployed, some intermediates of which are toxic, including a final step of coupling an isocyanate-containing siloxane with a modified amino acid. The end products, however, do not contain any free amino groups.

U.S. Pat. No. 5,516,869 discloses specific α,ω-amino acid-modified siloxanes which are synthesized by the hydrosilylating linking of alkenylpyrrolidones with α,ω-SiH-substituted siloxanes.

Another access point is the reaction, described in U.S. Pat. No. 5,412,074, of α,ω-epoxide-modified siloxanes with proteins, producing products whose siloxane units are connected to one another via polypeptide bridges of undefined length.

A similar access point is described by EP 1477512 A1, in which monoepoxysiloxanes are reacted with ε-polylysine. These structures have antimicrobial properties.

WO 2009084711 A1 describes the preparation of amino acid-modified siloxane emulsions. This publication gets around the divergent solubility properties of the epoxy-containing siloxanes and of the unprotected amino acids by performing the reaction in the presence of about 60% of water and 5% to 10% of emulsifiers. The emulsions have been tested in cosmetic applications.

The methods used in the prior art to couple amino acids or peptides to siloxanes involve reactions including epoxide ring-opening reactions, esterifications and transesterifications, amidations and substitution reactions. The disadvantages of the multi-stage processes described in the prior art include the use of toxic and difficult-to-manage raw materials, the use of expensive amino acid derivatives, the requirement for high temperatures, in some cases together with long reaction times, secondary reactions leading to discoloration and crosslinking, and low yields, as in reactions in emulsions, for example.

SUMMARY OF THE INVENTION

In aspect of the present invention, a process for preparing amino acid-modified siloxanes that can be carried out under mild conditions is provided.

In another aspect of the present invention, organically modified silicones for care formulations for skin, hair and textiles that are toxicologically unobjectionable are provided.

DETAILED DESCRIPTION OF THE INVENTION

The present invention provides a process for preparing siloxanes containing amino acid groups, by reaction of an organic amino acid salt with siloxanes containing epoxy groups and/or carbonate groups.

An advantage of the present process is the avoidance of expensive amino acid derivatives. Another advantage of the process of the present invention is the avoidance of toxic solvents. A further advantage of the process of the invention lies in the short reaction time of the process steps.

In addition, the process of the present invention represents a significant simplification relative to the prior-art processes, some of which have to be carried out at high temperatures, leading to strongly coloured products.

One feature of the process of the present invention for preparing siloxanes containing amino acid groups is that an amino acid is converted efficiently into an amino acid salt, which is subsequently reacted with a siloxane containing epoxy groups and/or carbonate groups, in the presence of a suitable solvent.

Notably, the present invention provides a process for preparing amino acid-modified siloxanes, comprising the process steps of:

C) reacting a salt of the general formula $K^+ A^-$ with at least one siloxane having at least one epoxy group and/or carbonate group, where $K^+$ is an organic cation and is the carboxylate of an α-aminocarboxylic acid, optionally D) reacting with a further organic component, containing epoxy groups, and optionally E) purifying the amino acid-modified siloxane.

The term "amino acid-modified siloxane" in the context of the present invention refers to a siloxane which comprises at least one group formed by the formation of a covalent bond to an amino acid.

The term "organic cation" in the context of the present invention refers to organic compounds which are positively charged in their overall net charge.

The term "carbonate group" in the context of the present invention refers to a group of the structure

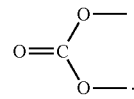

It is preferred in accordance with the present invention for the organic cation $K^+$ to comprise compounds having an ammonium group (ammonium cations) or having a phosphonium group (phosphonium cations).

The term "ammonium cations" refers in the context of the present invention to non-aromatic compounds with a localized positive charge on the nitrogen atom, examples include compounds with tetravalent nitrogen (quaternary ammonium compounds) or compounds with trivalent nitrogen, where one bond is a double bond, or aromatic compounds with a delocalized positive charge and at least one, preferably one to three, nitrogen atom(s) in the aromatic ring system.

The term "phosphonium cations" refers in the context of the present invention to non-aromatic compounds with a localized positive charge on the phosphorus atom, examples include compounds with tetravalent phosphorus (quaternary phosphonium compounds) or compounds with trivalent phosphorus, where one bond is a double bond.

Suitable organic cations $K^+$ are, for example, those of the general formula I:

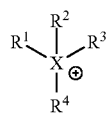

general formula I in which $R^1$, $R^2$, $R^3$ and $R^4$
are identical or different and are
a linear or branched, optionally double bond-containing aliphatic hydrocarbon radical with 1 to 30 carbon atoms,
an optionally double bond containing a cycloaliphatic hydrocarbon radical with 5 to 40 carbon atoms,
an aromatic hydrocarbon radical with 6 to 40 carbon atoms, an alkylaryl radical with 7 to 40 carbon atoms,
a linear or branched, optionally double bond-containing aliphatic hydrocarbon radical with 2 to 30 carbon atoms interrupted by one or more heteroatoms (e.g., oxygen, NH, NR' where R' is an optionally double bond-containing C1 to C30 alkyl radical, in particular —$CH_3$),
a linear or branched, optionally double bond-containing aliphatic hydrocarbon radical having from 2 to 30 carbon atoms, which is interrupted by one or more functionalities selected from the group of —O—C(O)—, —(O)C—O—, —NH—C(O)—, —(O)C—NH, —($CH_3$)N—C(O)—, —(O)C—N($CH_3$)—, —S($O_2$)—O—, —O—S($O_2$)—, —S($O_2$)—NH—, —NH—S($O_2$)—, —S($O_2$)—N($CH_3$)—, —N($CH_3$)—S($O_2$)—,
a terminally OH, OR', $NH_2$, N(H)R', N(R')$_2$ (where R' is an optionally double bond-containing C1 to C30 alkyl radical) functionalized linear or branched optionally double bond-containing aliphatic or cycloaliphatic hydrocarbon radical with 1 to 30 carbon atoms or
a blockwise or randomly constructed polyether according to —($R^5$—O)$_n$—$R^6$, where $R^5$ is a linear or branched hydrocarbon radical containing 2 to 4 carbon atoms, n is 1 to 100, preferably 2 to 60, and $R^6$ is hydrogen, a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, or a radical —C(O)—$R^7$ where $R^7$ is a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, and X is nitrogen or phosphorus, preferably nitrogen.

In one embodiment of the present invention, it is especially preferred for $R^1$, $R^2$, $R^3$ and $R^4$ to be identical or different and to be a linear or branched aliphatic hydrocarbon radical with 1 to 30 carbon atoms, with the proviso that at least one of the radicals $R^1$, $R^2$, $R^3$ and $R^4$ has 4 to 30 carbon atoms, preferably 8 to 26 carbon atoms, more preferably 10 to 22 carbon atoms.

Further suitable organic cations $K^+$ derive from saturated or unsaturated cyclic compounds and also from aromatic compounds having in each case at least one trivalent nitrogen atom in a 4- to 10-, preferably 5- to 6-membered heterocyclic ring, which may optionally be substituted. Such organic cations $K^+$ may be described in simplified form (i.e., without specification of precise position and number of the double bonds in the molecule) by the general formula II below, where the heterocyclic rings may optionally also contain a plurality of heteroatoms.

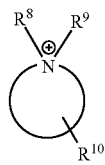

general formula II with
$R^8$ and $R^9$, identical or different, being as abovementioned $R^1$, $R^2$, $R^3$, $R^4$, and
$R^{10}$ being hydrogen, linear or branched optionally double bond-containing aliphatic hydrocarbon radical with 1 to 30 carbon atoms,
a cycloaliphatic optionally double bond-containing hydrocarbon radical with 5 to 40 carbon atoms,
an aromatic hydrocarbon radical with 6 to 40 carbon atoms or
an alkylaryl radical with 7 to 40 carbon atoms.

Examples of cyclic nitrogen compounds of the aforementioned kind are pyrrolidine, dihydropyrrole, pyrrole, imidazoline, oxazoline, oxazole, thiazoline, thiazole, isoxazole, isothiazole, indole, carbazole, piperidine, pyridine, the isomeric picolines and lutidines, quinoline and isoquinoline.

The cyclic nitrogen compounds of general formula II may be unsubstituted ($R^{10}$=H), substituted singly or else multiply by the radical $R^{10}$, and in the case of multiple substitution by $R^{10}$, the individual radicals $R^{10}$ may be different.

Further contemplated as other suitable organic cations $K^+$ are ions which derive from saturated acyclic, saturated or unsaturated cyclic compounds and also from aromatic compounds having in each case more than one trivalent nitrogen atom in a 4- to 10-, preferably 5- to 6-membered heterocyclic ring. These compounds may be substituted both on the carbon atoms and on the nitrogen atoms. These compounds may also be fused by optionally substituted benzene rings and/or cyclohexane rings, to form polycyclic structures. Examples of such compounds are pyrazole, 3,5-dimethylpyrazole, imidazole, benzimidazole, N-methylimidazole, dihydropyrazole, pyrazolidine, pyridazine, pyrimidine, pyrazine, pyridazine, pyrimidine, 2,3-, 2,5- and 2,6-dimethylpyrazine, cinnoline, phthalazine, quinazoline, phenazine and piperazine. In particular, organic cations of general formula III that are derived from imidazole and from its alkyl and phenyl derivatives have proved to be suitable as a constituent of organic salts.

Further contemplated as organic cations $K^+$ are ions which contain two nitrogen atoms and are represented by the general formula III

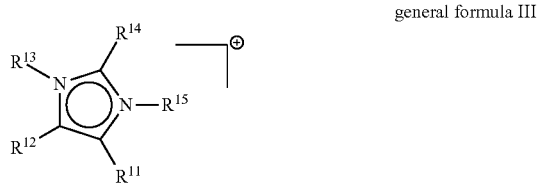

general formula III in which $R^{11}$, $R^{12}$, $R^{13}$, $R^{14}$ and $R^{15}$ are identical or different and are hydrogen, a linear or branched, optionally double bond-containing aliphatic hydrocarbon radical with 1 to 30 carbon atoms, a cycloaliphatic, optionally double bond-containing hydrocarbon radical with 5 to 40 carbon atoms, an aromatic hydrocarbon radical with 6 to 40 carbon atoms, an alkylaryl radical with 7 to 40 carbon atoms, a linear or branched, optionally double bond-containing aliphatic hydrocarbon radical with 1 to 30 carbon atoms interrupted by one or more heteroatoms (oxygen, NH, NR' where R' is an optionally double bond-containing $C_1$ to $C_{30}$ alkyl radical), a linear or branched, optionally double bond-containing aliphatic hydrocarbon radical having from 1 to 30 carbon atoms, which is interrupted by one or more functionalities selected from the group of —O—C(O)—, —(O)C—O—, —NH—C(O)—, —(O)C—NH, —(CH$_3$)N—C(O)—, —(O)C—N(CH$_3$)—, —S(O$_2$)—O—, —O—S(O$_2$)—, —S(O$_2$)—NH—, —NH—S(O$_2$)—, —S(O$_2$)—N(CH$_3$)—, —N(CH$_3$)—S(O$_2$)—, a terminally OH, OR', NH$_2$, N(H)R', N(R')$_2$, where R' is an optionally double bond-containing $C_1$ to $C_{30}$ alkyl radical, functionalized linear or branched optionally double bond-containing aliphatic or cycloaliphatic hydrocarbon radical with 1 to 30 carbon atoms or a blockwise or randomly constructed polyether according to —(R$_5$—O)$_n$—R$_6$, where $R^5$ is a hydrocarbon radical containing 2 to 4 carbon atoms, n is 1 to 100 and $R^6$ is hydrogen, a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, or a radical —C(O)—R$^7$ where $R^7$ is a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms.

As the carboxylate of an α-aminocarboxylic acid A$^-$, it is possible to use all carboxylates in which there is an amino group in alpha-position to the carboxyl group. Such compounds may include, for example, amino acids, proteins, peptides or oligopeptides.

As the carboxylate of an α-aminocarboxylic acid A$^-$, use is more particularly made of carboxylates of the α-aminocarboxylic acids selected from L-α-aminocarboxylic acids, preferably selected from the 22 proteinogenic amino acids, which may optionally be glycosylated, selected from glycine, alanine, valine, leucine, isoleucine, proline, methionine, phenylalanine, tyrosine, tryptophan, serine, threonine, asparagine, glutamine, cysteine, lysine, arginine, histidine, aspartate, selenocysteine, pyrrolysine and glutamate, especially preferably lysine, arginine and histidine.

As the carboxylate of α-aminocarboxylic acid A$^-$, it is also possible to use carboxylates of sarcosine, γ-aminobutyric acid, ornithines, creatine, opine, cystine, hydroxyproline, hydroxylysine, thyroxine and O-phophoserine.

In the process of the present invention use may be made of siloxanes which have at least one epoxy and/or carbonate group and in which the epoxy and/or carbonate groups are arranged purely terminally, purely pendently or as a mixture of both terminally and pendently in the siloxane. Use may also be made of cyclic siloxanes having at least one epoxy and/or carbonate group.

In the process of the present invention, preference is given to using siloxanes which have at least one epoxy group and/or carbonate group, and are of general formula IV $$M_{a1}M^A{}_{a2}M^B{}_{a3}D_{b1}D^A{}_{b2}D^B{}_{b3}T_{c1}T^A{}_{c2}T^B{}_{c3}Q_{d1} \quad \text{general formula IV}$$

with $M=[R^{16}{}_3SiO_{1/2}]$
$M^A=[R^{17}R^{16}{}_2SiO_{1/2}]$
$M^B=[R^{18}R^{16}{}_2SiO_{1/2}]$
$D=[R^{16}{}_2SiO_{2/2}]$
$D^A=[R^{17}{}_1R^{16}{}_1SiO_{2/2}]$
$D^B=[R^{18}{}_1R^{16}{}_1SiO_{2/2}]$
$T=[R^{16}SiO_{3/2}]$
$T^A=[R^{17}SiO_{3/2}]$
$T^B=[R^{18}SiO_{3/2}]$
$Q=[SiO_{4/2}]$ where $R^{16}$ independently at each occurrence is identical or different linear or branched, saturated or unsaturated hydrocarbon radicals having 1 to 30 carbon atoms or else aromatic hydrocarbon radicals having 6 to 30 carbon atoms, preferably methyl or phenyl, in particular methyl, $R^{17}$ independently at each occurrence is identical or different radicals containing epoxy groups and/or carbonate groups, $R^{18}$ independently at each occurrence is identical or different linear or branched, saturated or olefinically unsaturated hydrocarbon radicals with 8 to 30 carbon atoms, for example decyl, dodecyl, tetradecyl, hexadecyl, octadecyl, in particular hexadecyl and octadecyl, an aromatic hydrocarbon radical with 6 to 40 carbon atoms, an alkylaryl radical with 7 to 40 carbon atoms, a linear or branched, optionally double bond-containing aliphatic hydrocarbon radical with 2 to 30 carbon atoms interrupted by one or more heteroatoms (oxygen, NH, NR' where R' is an optionally double bond-containing C1 to C30 alkyl radical, in particular —CH$_3$), a linear or branched, optionally double bond-containing aliphatic hydrocarbon radical having from 2 to 30 carbon atoms, which is interrupted by one or more functionalities selected from the group of —O—C(O)—, —(O)C—O—, —NH—C(O)—, —(O)C—NH, —(CH$_3$)N—C(O)—, —(O)C—N(CH$_3$)—, —S(O$_2$)—O—, —O—S(O$_2$)—, —S(O$_2$)—NH—, —NH—S(O$_2$)—, —S(O$_2$)—N(CH$_3$)—, —N(CH$_3$)—S(O$_2$)—, a terminally OH, OR', NH$_2$, N(H)R', N(R')$_2$ (where R' is an optionally double bond-containing C1 to C30 alkyl radical) functionalized linear or branched optionally double bond-containing aliphatic or cycloaliphatic hydrocarbon radical with 1 to 30 carbon atoms or a blockwise or randomly constructed polyether according to —(R$^5$—O)$_n$—R$^6$, where R$^5$ is a linear or branched hydrocarbon radical containing 2 to 4 carbon atoms, n is 1 to 100, preferably 2 to 60, and R$^6$ is hydrogen, a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, or a radical —C(O)—R$^7$, where R$^7$ is a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, a1=0 to 200, preferably 1 to 60, more particularly 0,
a2=0 to 30, preferably 1 to 20, more particularly 2 to 10,
a3=0 to 30, preferably 1 to 20, more particularly 0,
b1=3 to 5000, preferably 3 to 1000, more particularly 10 to 500,
b2=0 to 100, preferably 1 to 30, more particularly 1 to 10,
b3=0 to 100, preferably 0 to 30, more particularly 0,
c1=0 to 30, preferably 1 to 30, alternatively preferably 0,
c2=0 to 30, preferably 0 to 10, more particularly 0 to 5,
c3=0 to 30, preferably 0 to 5, more particularly 0,
d1=0 to 30, preferably 1 to 5, alternatively preferably 0,
with the proviso that at least one of the indices a2, b2 or c2≠0.

Siloxanes with at least one epoxy group which are preferred in accordance with the present invention and employed in the process are characterized by the parameter coding selected from the following group:
a1=0, a2=2, a3=0, b1=5-350, b2=0, b3=0, c1=0, c2=0, c3=0 and d1=0,
a1=3-12, a2=0, a3=0, b1=15-350, b2=0, b3=0, c1=0, c2=1-10, c3=0 and d1=0,
a1=2, a2=0, a3=0, b1=10-350, b2=1-30, b3=0, c1=0, c2=0, c3=0 and d1=0,
a1=0, a2=2, a3=0, b1=10-350, b2=1-30, b3=0, c1=0, c2=0, c3=0 and d1=0,
a1=0, a2=3-12, a3=0, b1=15-350, b2=0, b3=0, c1=1-10, c2=0, c3=0 and d1=0,
a1=0, a2=4-22, a3=0, b1=20-350, b2=0, b3=0, c1=0, c2=0, c3=0 and d1=1-10,
a1=2-11, a2=2-11, a3=0, b1=20-350, b2=0, b3=0, c1=0, c2=0, c3=0 and d1=1-10,
a1=2-11, a2=2-11, a3=0, b1=20-350, b2=1-10, b3=0, c1=0, c2=0, c3=0 and d1=1-10,
a1=0, a2=3-12, a3=0, b1=15-350, b2=1-10, b3=0, c1=1-10, c2=0, c3=0 and d1=0,
a1=3-12, a2=0, a3=0, b1=15-350, b2=1-10, b3=0, c1=0, c2=1-10, c3=0 and d1=0,
a1=0, a2=5-17, a3=0, b1=30-350, b2=0, b3=0, c1=1-5, c2=0, c3=0 and d1=1-5 and
a1=0, a2=0, a3=0, b1=0-10, b2=1-10, b3=0, c1=0, c2=0, c3=0 and d1=0.

It is preferred in accordance with the present invention for siloxanes to be used in the process, having at least one epoxy group and/or carbonate group, in which the epoxy group-containing radicals R$^{17}$ correspond to general formula Va, and the carbonate group-containing radicals R$^{17}$ correspond to general formula Vb

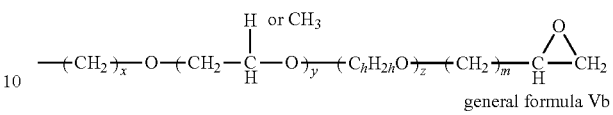
general formula Va

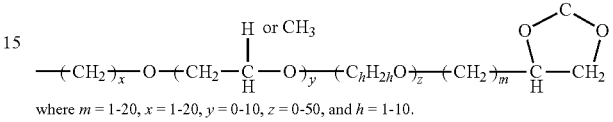
general formula Vb where $m = 1\text{-}20, x = 1\text{-}20, y = 0\text{-}10, z = 0\text{-}50,$ and $h = 1\text{-}10.$ In process step C), in accordance with the present invention, a solvent may be used, such as, for example, water, acetone, acetonitrile, tert-butanol, chloroform, dichloromethane, acetic acid, bis(2-methoxyethyl)ether, dimethylacetamides, ethanol, ethylene glycol, dipropylene glycol, methanol, isopropanol, diethyl ether, pyridine, dimethyl sulphoxide, dimethylformamide, polyethers and mixtures thereof.

Especially preferred is the use in process step C) of protic solvents, which are able at least in part to comprise water.

The pH of the solvent in process step C) at 25° C. is preferably in a range from 1 to 14, preferably from 3 to 9, more particularly from 5 to 7.

In an alternative but no less preferred embodiment it is possible in process step C) to operate with at least two solvents, which form a multi-phase system.

Systems of this kind comprising at least two solvents forming a multi-phase system include, for example, at least one component selected from water, chloroform, diethyl ether, dichloromethane, toluene and xylene.

Process step C) of the process of the present invention can be carried out in a temperature range from 20 to 200° C., preferably from 40 to 120° C., especially preferably from 60 to 100° C.

Process step C) of the process of the present invention can be carried out in a pressure range from 0 to 20 bar, preferably 0 to 2 bar, especially preferably at 0.9 to 1.1 bar.

Process step C) of the process of the present invention may be carried out either with inertization using noble gases such as argon, for example, or else under nitrogen or under conventional atmosphere. Particularly preferred is its implementation under inert gas, in which case nitrogen is particularly preferred.

The reaction mixture can be obtained by arbitrary mixing of the components. It is immaterial here which component is added in which order.

Process step C) of the process of the present invention can be carried out either as a one-pot process (batch process) or else with metering of the raw materials. In the latter case, preference is given to introducing the salt of the general formula K$^+$ A$^-$ to start with, and metering in the siloxane having at least one epoxy group, optionally in a solvent, over a period of 0.5-2 hours.

With particular preference, the starting materials and any solvents are mixed first of all.

Preferred in accordance with the present invention is a duration for process step C) of less than 10 hours.

Process step C) of the process of the present invention is carried out preferably in a batch process.

Furthermore, the resulting amino acid-containing siloxane may be reacted with a further epoxy-containing organic component, in process step D). The organic epoxidic compounds here may be monomeric or polymeric in nature. Preference here is given to polyether-containing and aromatic epoxides.

The reaction in process step D) is the same in terms of its conditions to the reaction in process step C).

It is preferred in accordance with the present invention if the salt of the general formula $K^+ A^-$ for process step C) of the process of the present invention is provided via the additional process steps A) and B) as described below. A preferred process of the invention is therefore characterized in that it comprises the additional process steps of
  A) reacting an α-aminocarboxylic acid $H^+A^-$ with an organic salt of an organic cation $K^+$ in the presence of a base to give a salt of the general formula $K^+ A^-$,
and optionally
  B) purifying the salt of general formula $K^+ A^-$.

It is obvious that as "α-aminocarboxylic acid $H^+A^-$" to be used in step A) it is necessary to employ the corresponding acid of the "carboxylate of an α-aminocarboxylic acid $A^-$" of process step C).

In process step A), the α-aminocarboxylic acid $H^+A^-$ may be used in the form of its adducts and/or salts, such as hydrates, hydrochlorides and acetates, for example. These may also be used in the form of an aqueous solution.

The "α-aminocarboxylic acid $H^+A^-$" for use in process step A) is therefore provided by the combination of the "carboxylate of an α-aminocarboxylic acid $A^-$" specified in process step C) with a proton, using as "α-aminocarboxylic acid $H^+A^-$" in process step A) "α-aminocarboxylic acids $H^+A^-$" of process step C) specified as preferred" above, preferably in combination with a proton.

It is obvious that as "organic salt of an organic cation $K^+$" for use in process step A) it is necessary to use the corresponding salt of the "organic cation $K^+$" specified in process step C).

The "organic salt of an organic cation $K^+$" for use in process step A) is therefore provided from the combination of the "organic cation $K^+$" specified in process step C) with an anion, using as "organic salt of an organic cation $K^+$" in process step A) "organic cations $K^+$ of process step C) specified as preferred" above, preferably in combination with an anion.

Preferred counter-anions of the organic salt of the organic cation $K^+$ in process step A) in this context are selected from the group of halides, hydroxides, bis(perfluoroalkylsulphonyl)amides, alkyl- and aryltosylates, perfluoroalkyltosylates, nitrates, sulphates, hydrogensulphates, alkyl- and arylsulphates, polyether sulphates and sulphonates, perfluoroalkylsulphates, sulphonates, alkyl- and arylsulphonates, perfluorinated alkyl- and arylsulphonates, alkyl- and arylcarboxylates, perfluoroalkylcarboxylates, perchlorates, tetrachloroaluminates, saccharinates, dicyanamide, tetrafluoroborate, hexafluorophosphate, polyether-phosphates and phosphate, with hydroxides being preferred in accordance with the present invention.

As a base it is possible in process step A) to use organic and inorganic bases. Examples of inorganic bases are alkali metal and alkaline earth metal hydroxides such as sodium hydroxide, potassium hydroxide, calcium hydroxide, barium hydroxide, etc. Examples of organic bases are alkoxides of the alkali metals or alkaline earth metals, ammonium hydroxides and phosphonium hydroxides. Preference is given to using alkali metal and alkaline earth metal hydroxides.

Process step A) of the process of the invention may in accordance with the present invention be carried out in the presence of a solvent. Examples of such are water, acetone, acetonitrile, tert-butanol, chloroform, dichloromethane, acetic acid, bis(2-methoxyethyl) ether, dimethylacetamides, ethanol, ethylene glycol, methanol, isopropanol, diethyl ether, pyridine, dimethyl sulphoxide, dimethylformamide, polyethers and mixtures thereof.

In process step A) of the process of the present invention, preference is given to using protic solvents, which may at least in part comprise water. More particularly the solvent may be water.

The pH of the solvent in process step A) at 25° C. is preferably in a range from 1 to 14, preferably from 3 to 14, more particularly 5 to 12.

Process step A) of the process of the present invention can be carried out in a temperature range from 20 to 200° C., preferably from 20 to 120° C., especially preferably from 40 to 100° C.

Process step A) of the process of the present invention can be carried out in a pressure range from 0 to 20 bar, preferably 0 to 2 bar, especially preferably at 0.9 to 1.1 bar.

Process step A) of the process of the present invention may be carried out either with inertization using noble gases such as argon, for example, or else under nitrogen or under conventional atmosphere. Particularly preferred is its implementation under inert gas, in which case nitrogen is particularly preferred.

The reaction mixture can be obtained by arbitrary mixing of the components. It is immaterial here which component is added in which order.

Process step A) of the process of the present invention can be carried out either as a one-pot process (batch process) or else with metering of the raw materials.

Preferred in accordance with the present invention is a duration for process step B) of the process of the invention of 2 to 24 hours.

It may be advantageous if in process step B) of the process of the present invention, by-products are removed from the reaction mixture. Such by-products may, in particular, be those obtained by salt exchange. Such by-products are preferably alkali metal and alkaline earth metal halides, resulting, for example, from the use of alkali metal hydroxides as base and quaternary ammonium halides as exchange salt. The removal of the by-products, more particularly the alkali metal and alkaline earth metal halides, may be accomplished, for example, by a simple filtration. The solid may be removed in a conventional way from the reaction mixture. The solid can be separated from the reactor mixture preferably by filtration. The filtration may be performed either with or without application of reduced pressure. Filter materials used may include, for example, cellulosic depth filters. Preference is given to using plate filters with cellulose, perlite, kieselguhr, zeolite and activated carbon as filter material.

In some embodiments, it may be necessary for the solvent used to be removed in process step B) of the process of the present invention. For this purpose a simple distillation of the solvent can be employed. In the case of water, freeze-drying may alternatively also be carried out in process step B) of the process of the present invention.

The distillation in process step B) of the process of the present invention takes place preferably at a liquid-phase temperature (temperature of the reaction mixture) of 50° C. to 200° C., more preferably 50° C. to 150° C., especially preferably 80° C. to 120° C., and under a pressure of 0.1 to 1013 mbar, more preferably >0.1 to 100 mbar, especially >0.1 to 20 mbar.

A further subject of the present invention is the intermediate in the process of the present invention, as described below. This intermediate is suitable with particular advantage for being reacted in process step C).

This further subject of the present invention is therefore a salt of the general formula $K^+ A^-$ with
$K^+$ being an organic cation and
being the carboxylate of an α-aminocarboxylic acid, characterized in that
$K^+$ is a compound comprising an ammonium group which has at least one organic radical with 8 to 30 carbon atoms, preferably 12 to 26 carbon atoms, more preferably 16 to 22 carbon atoms.

Preferred salts of the present invention are those which as organic cation $K^+$ feature compounds of general formula I with X=nitrogen, II or III, as described above in connection with the process of the present invention.

Particularly preferred salts of the present invention are characterized in that the organic cation $K^+$ features a compound of general formula I

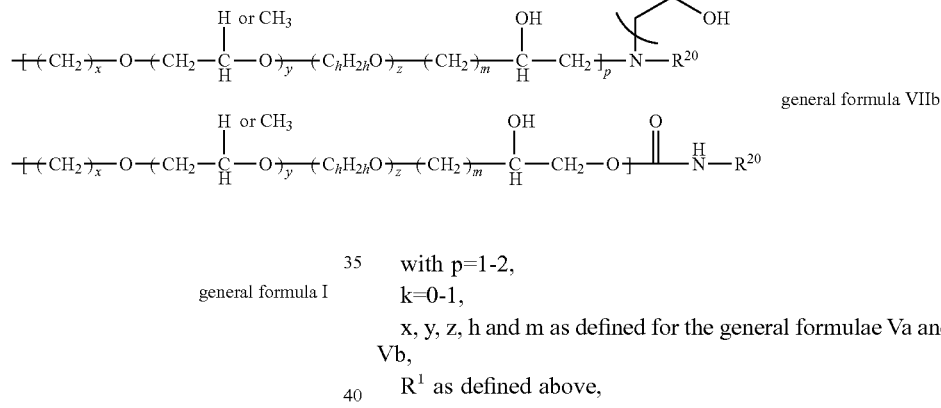

general formula I with X=nitrogen and $R^1$, $R^2$, $R^3$ and $R^4$, identically or differently, being linear or branched aliphatic hydrocarbon radical with 1 to 30 carbon atoms, with the proviso that at least one of the radicals $R^1$, $R^2$, $R^3$ and $R^4$ has 4 to 30 carbon atoms, preferably 8 to 26 carbon atoms, more preferably 10 to 22 carbon atoms.

Preferred salts of the present invention are those which as the carboxylate of an α-aminocarboxylic acid $A^-$ feature carboxylates of the acids selected from L-α-aminocarboxylic acids, preferably selected from the 22 proteinogenic amino acids, which may optionally be glycosylated, selected from glycine, alanine, valine, leucine, isoleucine, proline, methionine, phenylalanine, tyrosine, tryptophan, serine, threonine, asparagine, glutamine, cysteine, lysine, arginine, histidine, aspartate, selenocysteine, pyrrolysine and glutamate, especially preferably lysine, arginine and histidine.

Also, salts which as the carboxylate of an α-aminocarboxylic acid $A^-$ feature carboxylates of the acids selected from sarcosine, γ-aminobutyric acid, ornithines, creatine, opine, cystine, hydroxyproline, hydroxylysines, thyroxine and O-phophoserine are alternatively preferred.

A further subject is a siloxane obtainable by the process of the present invention.

Alternative siloxanes of the present invention are characterized in particular by general formula VI $$M_{a1}M^C{}_{a2}M^B{}_{a3}D_{b1}D^C{}_{b2}D^B{}_{b3}T_{c1}T^C{}_{c2}T^B{}_{c3}Q_{d1} \quad \text{general formula VI}$$

with
$M=[R^{16}{}_3SiO_{1/2}]$
$M^C=[R^{19}R^{16}{}_2SiO_{1/2}]$
$M^B=[R^{18}R^{16}{}_2SiO_{1/2}]$
$D=[R^{16}{}_2SiO_{2/2}]$
$D^C=[R^{19}{}_1R^{16}{}_1SiO_{2/2}]$
$D^B=[R^{18}{}_1R^{16}{}_1SiO_{2/2}]$
$T=[R^{16}SiO_{3/2}]$
$T^C=[R^{19}SiO_{3/2}]$
$T^B=[R^{18}SiO_{3/2}]$
$Q=[SiO_{4/2}]$,
where
a1, a2, a3, b1, b2, b3, c1, c2, c3, d1, $R^{16}$ and $R^{18}$ as defined above,
$R^{19}$ independently at each occurrence is identical or different radicals of the general formula VIIa and/or VIIb

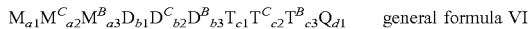
general formula VIIa

general formula VIIb

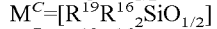

with p=1-2,
k=0-1,
x, y, z, h and m as defined for the general formulae Va and Vb,
$R^1$ as defined above,

coding derives from above-defined $K^+ A^-$, which is bonded with loss of an H to an amino group with the radical $R^{19}$ and

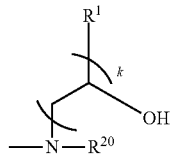

coding derives from coding

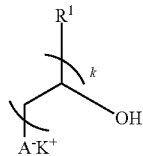

with $K^+ A^-$, as defined above, which is bonded with loss of an H to an amino group with the radical $R^{19}$.

For the sake of completeness it may be stated that the amino group forming the covalent bond need not necessarily be the alpha-amino group; accordingly, as in the case of lysine, for example, the epsilon-amino group may also form the corresponding bond. In principle, therefore, there may be crosslinking reactions even when two or more amino groups are present in $A^-$.

Preferred radicals $R^{20}$ result from the preferred $K^+$ and $A^-$ described above for the process of the present invention.

Preferred parameters and parameter combinations for a1, a2, a3, b1, b2, b3, c1, c2, c3, d1, $R^{16}$ and $R^{18}$ are those as described above for the process of the present invention.

A further subject of the present invention is the use of the siloxanes of the present invention and/or of the siloxanes obtainable by the process of the present invention for producing formulations, more particularly cosmetic or pharmaceutical formulations and also care formulations and cleaning formulations for application in the domestic and industrial spheres. In this context, preferred cosmetic or pharmaceutical formulations are, in particular, skin and hair treatment formulations, more particularly hair conditioning formulations. Preferred care and cleaning formulations for application in the domestic and industrial spheres are, in this context, fabric care compositions, such as softeners, for example, and polishes for hard surfaces, particularly for vehicles, watercraft, aircraft, window panes and window sills, shower partitions, flooring such as carpets, tiles, laminates, woodblock, cork floors, marble, stone and fine stoneware floors, household ceramics such as WCs, basins, bidets, shower trays, bathtubs, door handles, fittings, household appliances such as washing machines, driers, dishwashers, ceramic or stainless steel sinks, furniture such as tables, chairs, shelving, storage surfaces, windows, kitchenware, tableware and cutlery, tools such as surgical instruments, vacuum cleaners, machines, pipelines, tanks and apparatus for transport, processing and storage in food processing, such as rinse aids, for example.

The present invention accordingly further provides formulations, more particularly cosmetic or pharmaceutical formulations and care and cleaning formulations for application in the domestic and industrial spheres, comprising siloxanes obtainable by the process of the present invention, more particularly in an amount of 0.1 to 7 wt %, preferably 0.5 to 4 wt %, more preferably 1 to 3 wt %, based on the overall formulation, especially aqueous formulations which preferably have a pH of 3.5 to 5.5.

Preferred formulations of the present invention contain no further siloxanes.

The term "aqueous" in this context refers to a water content of greater than 50 wt %, preferably greater than 75 wt %, based on the overall formulation.

The present invention further provides for the use of the siloxanes of the present invention and/or of the siloxanes obtainable by the process of the present invention or of the formulations of the present invention for the conditioning of a surface, preferably of fibres or fabrics, more particularly of skin, hair or textiles.

The examples adduced below illustrate the present invention by way of example, without any intention of restricting the invention, the scope of application of which is apparent from the entirety of the description and the claims, to the embodiments specified in the examples.

EXAMPLES

Preparation of the Amino Acid-Modified and Peptide-Modified Siloxanes of the Invention The recording and interpretation of NMR spectra is known to the skilled person. Introduced hereby as a reference is the book "NMR Spectra of Polymers and Polymer Additives" by A. Brandolini and D. Hills, published in 2000 by Marcel Dekker Inc.

GPC measurements for determining the polydispersity and average molar mass Mw were carried out under the following measurement conditions: column combination SDV 1000/10000 Å (length 65 cm), temperature 30° C., THF as mobile phase, flow rate 1 ml/min, sample concentration 10 g/l, RI detector, polymers evaluated against polystyrene standard (162 2 570 000 g/mol).

Synthesis Example S1

Preparation of Cetyltrimethylammonium Arginate 74.3 g (0.42 mol) of arginine (from SAFC, 98.5% purity) was suspended in water in a 1 l four-necked flask with internal thermometer, KPG stirrer and bulb condenser. Subsequently 23.5 g (0.42 mol) of potassium hydroxide (from J.T. Baker, 100% purity) was dissolved in 23.5 g of water, this solution was added to the flask with stirring, and the mixture was stirred at room temperature for 30 minutes. Thereafter the solution was heated to 80° C. and 422.3 g (0.42 mol) of cetyltrimethylammonium chloride (from Evonik Industries AG, 30% in water) was added, with stirring at 80° C. for two hours more and additionally at room temperature overnight. The water was distilled off with application of a reduced pressure at 60° C. The resulting product was dissolved in tert-butanol (from Sigma Aldrich, >97.8%) and admixed with a little sodium sulphate, and the precipitate was isolated by filtration. The solvent was subsequently distilled off with application of a reduced pressure at 60° C.

The $^{13}$C NMR confirmed the preparation of a 1:1 salt of arginate and cetyltrimethylammonium.

Synthesis Example S2

Preparation of Cetyltrimethylammonium Lysinate 63.9 g (0.45 mol) of lysine (from ABCR, 97% purity) was suspended in water in a 1 l four-necked flask with internal thermometer, KPG stirrer and bulb condenser. Subsequently 25.8 g (0.42 mol) of potassium hydroxide (from J.T. Baker, 100% purity) was dissolved in 25.8 g of water, this solution was added to the flask with stirring, and the mixture was stirred at room temperature for 30 minutes. Thereafter the solution was heated to 80° C. and 460.2 g (0.45 mol) of cetyltrimethylammonium chloride (from Evonik Industries AG, 30% in water) was added, with stirring at 80° C. for two hours more and additionally at room temperature overnight. The water was distilled off with application of a reduced pressure at 60° C. The resulting product was dissolved in tert-butanol (from Sigma Aldrich, >97.8%) and admixed with a little sodium sulphate, and the resulting precipitate was isolated by filtration. The solvent was subsequently distilled off with application of a reduced pressure at 60° C.

The $^{13}$C NMR confirmed the preparation of a 1:1 salt of lysinate and cetyltrimethylammonium.

Synthesis Example S3

Preparation of Behenyltrimethylammonium Lysinate 48 g (0.32 mol) of lysine (from ABCR, 97% purity) was suspended in 56 g of ethanol in a 0.5 l four-necked flask with internal thermometer, KPG stirrer and bulk condenser. Subsequently 17.9 g (0.32 mol) of potassium hydroxide (from J.T. Baker, 100%) was dissolved in 40 g of ethanol, this solution was added to the reaction flask with stirring, and the mixture was stirred at room temperature for 30 minutes. Then the solution was heated to 80° C. and 150 g (0.32 mol) of behenyltrimethylammonium chloride (from Evonik Industries AG, 85% in isopropanol) in solution in 150 g of isopropanol was added. After two hours at 80° C., the solution was stirred at room temperature overnight. The resulting precipitate was removed by a simple filtration, and the solvent was distilled off with application of a reduced pressure at 60° C.

The $^{13}$C NMR confirmed the preparation of a 1:1 salt of lysine and behenyltrimethylammonium.

Synthesis Example S4

Reaction of α,ω-epoxysiloxane with N=80 with Behenyltrimethylammonium Lysinate 100 g (0.018 mol) of α,ω-epoxysiloxane (N=80, M=5517.2 g/mol, epoxy value: 0.58%, from Evonik Industries AG), 18.5 g (0.036 mol) of behenyltrimethylammonium lysinate from Synthesis Example S3 and 29.7 g of tert-butanol (from Sigma Aldrich, >97.8%) were introduced into a 0.25 l four-necked flask with internal thermometer, bulb condenser and KPG stirrer. The mixture was stirred at 85° C. for five hours. The solvent was then distilled off with application of a reduced pressure at 60° C.

$^1$H NMR and GPC confirmed the preparation of the amino acid-modified siloxane.

Synthesis Example S5

Reaction of α,ω-epoxysiloxane with N=80 with Cetyltrimethylammonium Lysinate 100 g (0.018 mol) of α,ω-epoxysiloxane (N=80, M=5517.2 g/mol, epoxy value: 0.58%, from Evonik Industries AG), 15.5 g (0.036 mol) of cetyltrimethylammonium lysinate from Synthesis Example S2 and 28.9 g of tert-butanol (from Sigma Aldrich, >97.8%) were introduced into a 0.25 l four-necked flask with internal thermometer, bulb condenser and KPG stirrer, and heated to 85° C. This mixture was stirred for five hours, after which the solvent was distilled off with application of a reduced pressure at 60° C.

$^1$H NMR and GPC confirmed the preparation of the amino acid-modified siloxane.

Synthesis Example S6

Reaction of α,ω-epoxysiloxane with N=80 with Cetyltrimethylammonium Arginate 100 g (0.018 mol) of α,ω-epoxysiloxane (N=80, M=5517.2 g/mol, epoxy value: 0.58%, from Evonik Industries AG), 15.9 g (0.036 mol) of cetyltrimethylammonium arginate from Synthesis Example S1 and 29 g of tert-butanol (from Sigma Aldrich, >97.8%) were introduced into a 0.25 l four-necked flask with internal thermometer, bulb condenser and KPG stirrer, and heated to 85° C., and stirred at this temperature for four hours. Subsequently the solvent was distilled off with application of a reduced pressure at 60° C.

$^1$H NMR and GPC confirmed the preparation of the amino acid-modified siloxane.

Synthesis Example S7

Reaction of a T-Structural Epoxysiloxane with N=150 and Cetyltrimethylammonium Arginate 50 g (0.0047 mol) of an epoxysiloxane (N=150, M=10 666 g/mol, epoxy value: 0.45%, from Evonik Industries AG), 6.2 g (0.014 mol) of cetyltrimethylammonium arginate from Synthesis Example S1 and 28 g of tert-butanol (from Sigma Aldrich, >97.8%) were charged to a 0.25 l four-necked flask with internal thermometer, bulb condenser and KPG stirrer, heated to 85° C. and stirred for four hours. Finally the solvent was distilled off with application of a reduced pressure at 60° C.

$^1$H NMR and GPC confirmed the preparation of the amino acid-modified siloxane.

Synthesis Example S8

Reaction of an α,ω-epoxysiloxane with N=30 and Cetyltrimethylammonium Arginate 50 g (0.021 mol) of an α,ω-epoxysiloxane (N=30, M=2335.8 g/mol, epoxy value: 1.37%, from Evonik Industries AG), 18.8 g (0.042 mol) of cetyltrimethylammonium arginate from Synthesis Example S1 and 17.2 g of tert-butanol (from Sigma Aldrich, >97.8%) were charged to 0.25 l four-necked flask with internal thermometer, bulb condenser and KPG stirrer. The mixture was heated to 85° C. and stirred at this temperature for four hours. The solvent was subsequently distilled off by application of a reduced pressure at 60° C.

$^1$H NMR and GPC confirmed the preparation of the amino acid-modified siloxane.

Synthesis Example S9

Preparation and Reaction of a Tetraepoxytetramethyltetracyclosiloxane with Cetyltrimethylammonium Arginate 123.66 g (1.08 mol) of allyl glycidyl ether (from Sigma Aldrich) was introduced in 123.66 g of toluene and heated to 80° C. 0.17 g of Karstedt catalyst (1% strength solution in cyclen, 10 ppm platinum based on the batch) was then added. 50 g (0.83 mol) of methylhydrocyclosiloxane (ABCR, 92%) in 25 g of toluene was added slowly dropwise. Regular volumetric Si—H conversion determination until 100% conversion. Then excess toluene and allyl glycidyl ether were distilled off under reduced pressure on a rotary evaporator at 100° C.

55.2 g (0.121 mol) of cetyltrimethylammonium arginate from Synthesis Example 1 and 55.2 g of tert-butanol (from Sigma Aldrich, >97.8%) were charged to a 0.25 l four-necked flask with bulb condenser and dropping funnel, and heated to 82° C. 21 g (0.121 mol) of the reaction product of allyl glycidyl ether and methylhydrocyclosiloxane were added slowly dropwise to 21 g of tert-butanol, with stirring for a further 2 hours. Finally, tert-butanol was distilled off on a rotary evaporator at 80° C.

$^1$H NMR confirmed the preparation of the amino acid-modified siloxane.

Synthesis Example S10

Preparation of Cetyltrimethylammonium Histidate 57.8 g (0.365 mol) of histidine (from ABCR, 98%) was suspended in water in a 1 l four-necked flask with internal thermometer, KPG stirrer and bulb condenser. 20.5 g (0.365 mol) of potassium hydroxide (from J.T. Baker, 100%), in solution in 20 g of water, was added to the flask with stirring, followed by stirring at room temperature for 30 minutes. The solution was then heated at 80° C. and 367.5 g (0.344 mol) of cetyltrimethylammonium chloride (from Evonik Industries AG, 30% strength in water) was added, and stirring took place at 80° C. for a further two hours and lastly at room temperature overnight. The water was distilled off with application of a reduced pressure at 60° C. The resulting amino acid salt was taken up in tert-butanol (from Sigma Aldrich, >97.8%) and sodium sulphate, and the precipitate formed was isolated by filtration. The pure salt was then obtained by distillation of tert-butanol.

$^{13}$C NMR confirmed the preparation of a 1:1 salt of histidate and cetyltrimethylammonium.

Synthesis Example S11

Preparation of Cetyltrimethylammonium Glutamate 73.5 g (0.498 mol) of glutamine (from Sigma Aldrich, 99%) was suspended in water in a 1 l four-necked flask with internal thermometer, KPG stirrer and bulb condenser. 27.9 g (0.498 mol) of potassium hydroxide (from J.T. Baker, 100% purity), in solution in 27.9 g of water, was then added to the flask with stirring, and stirring took place for 30 minutes, before the solution was heated to 80° C. and 500 g (0.468 mol) of cetyltrimethylammonium chloride (from Evonik Industries AG, 30% in water) was added. The solution was stirred at 80° C. for two hours more and then at room temperature overnight. The resulting amino acid salt was taken up in tert-butanol (from Sigma Aldrich, >97.8%) and sodium sulphate, and the precipitate formed was isolated by filtration. The pure salt was then obtained by distillation of tert-butanol.

$^{13}$C NMR confirmed the preparation of a 1:1 salt of glutamate and cetyltrimethylammonium.

Synthesis Example S12

Preparation of Trihexyltetradecylphosphonium Lysinate 6.9 g (0.046 mol) of lysine (from ABCR, 97%) was suspended in 20 g of ethanol in a 0.25 l four-necked flask with internal thermometer, KPG stirrer and bulb condenser, and then 2.6 g (0.046 mol) of potassium hydroxide (from J.T. Baker, 100%), in solution in 10 g of ethanol, was added with stirring, and the mixture was stirred for 30 minutes. The solution was then heated to 80° C. and 25 g (0.046 mol) of trihexyltetradecylphosphonium chloride (from Sigma Aldrich, 95%) in solution in 40 g of isopropanol was added. The solution was stirred at 80° C. for two hours more and then at room temperature overnight. The resulting precipitate was isolated by filtration and the solvent in the filtrate was distilled off at 60° C. with application of a reduced pressure.

$^{13}$C NMR confirmed the preparation of a 1:1 salt of lysinate and trihexyltetradecylphosphonium.

Synthesis Example S13

Preparation of 1-methyl-3-octylimidazolium lysinate 15.8 g (0.105 mol) of lysine (from ABCR, 97%) was suspended in 30 g of ethanol in a 0.25 l four-necked flask with internal thermometer, KPG stirrer and bulb condenser, and then 5.8 g (0.105 mol) of potassium hydroxide (from J.T. Baker, 100%), in solution in 10 g of ethanol, was added with stirring, and the mixture was stirred for 30 minutes. The solution was then heated to 80° C. and 25 g (0.105 mol) of 1-methyl-3-octylimidazolim chloride (from Sigma Aldrich, 97%), in solution in 30 g of isopropanol was added. The solution was stirred at 80° C. for two hours more and then at room temperature overnight. The resulting precipitate was isolated by filtration and the solvent in the filtrate was distilled off at 60° C. with application of a reduced pressure.

$^{13}$C NMR confirmed the preparation of a 1:1 salt of lysinate and 1-methyl-3-octylimidazolium.

Synthesis Example S14

Reaction of α,ω-Carbonate-Containing Siloxane with N=80 and Cetyltrimethylammonium Lysinate 6.9 g (0.016 mol) of cetyltrimethylammonium lysinate from Synthesis Example S2 and 14.3 g of tert-butanol (from Sigma Aldrich, >97.8%) were charged to a 0.25 l four-necked flask with internal thermometer, bulb condenser and KPG stirrer, this initial charge was heated to 85° C., and 50 g (0.008 mol) of an α,ω-carbonate-containing siloxane with N=80 (M=6224 g/mol), prepared as described in U.S. Pat. No. 5,606,077, were added dropwise over the course of 60 minutes. The reaction was stirred for a further nine hours. Finally the tert-butanol solvent was distilled off on a rotary evaporator at 60° C.

$^1$H NMR and $^{13}$C NMR confirmed the successful conversion to give the amino acid-carrying siloxane.

Synthesis Example S15

Reaction of α,ω-epoxysiloxane N=80 and Monoepoxypolyether with Cetyltrimethylammonium Arginate 100 g (0.018 mol) of α,ω-epoxysiloxane (N=80, M=5517.2 g/mol, epoxy value: 0.58% (from Evonik Industries AG), 15.9 g (0.036 mol) of cetyltrimethylammonium arginate from Synthesis Example S1 and 29 g of tert-butanol (from Sigma Aldrich, >97.8%) were heated to 85° C. in a 0.25 l four-necked flask with internal thermometer, bulb condenser and KPG stirrer, and was stirred at this temperature for four hours. Subsequently a monoepoxypolyether (ipox chemicals, epoxy equivalent: 470-500) was added, and stirring was continued at 80° C. for a further 2 hours. Finally the solvent was distilled off with application of a reduced pressure at 60° C.

Fabric Care Examples

The skilled person is aware that the application of textile assistants such as softeners, for example, can lead to surface hydrophobization. This surface hydrophobization is manifested in poorer rewetting of the textile by water. The copolymers of the present invention produce a distinct hydrophilization of textile fibres and are capable, even in combination with textile assistants that have adverse effects on the rewetting behavior, of achieving a marked reduction in the hydrophobization such assistants induce.

In order to verify the hydrophilicity achievable when using amino acid-containing siloxanes of the present invention on textile fibres, a variety of standard textiles were treated and were tested exemplarily against a commercially available active softener ingredient (Rewoquat WE18, Evonik Industries) in respect of its rewetting capabilities, by means of a wicking test.

Standard Textiles Used:

Cotton fabric wfl code 13A, polyester fabric wfk code 30A, both available from wfk Testgewebe GmbH, Krefeld.

Treatment of the Test Textile Specimens (Cotton) by Forced Application:

From a sheet of material, test textile specimens were cut that measured 25×7.5 cm and had a mass of 4 g. Treatment liquors consisting of the respective active ingredients (0.077 wt %) in water (16° dH [German hardness]) were then prepared in 1 l plastic PE bottles. The liquors thus prepared were stirred for 2 hours to ensure homogeneous incorporation of the active ingredient. The individual test textile specimens were then wetted with 13.7 g of the above-prepared liquor solution, in a Teflon beaker, and were agitated in the liquor using a polyethylene spatula. After exactly 10 minutes, the test specimens were removed from the liquor, fixed to a line to dry, and not measured until the following day.

Treatment of the Test Textile Specimens (Polyester) by Forced Application:

From a sheet of material, test textile specimens were cut that measured 25×7.5 cm and had a mass of 3 g. Treatment liquors consisting of the respective active ingredients (0.077 wt %) in water (16° dH [German hardness]) were then prepared in 1 l plastic PE bottles. The liquors thus prepared were stirred for 2 hours to ensure homogeneous incorporation of the active ingredient. The individual test textile specimens were then wetted with 10.3 g of the above-prepared liquor solution, in a Teflon beaker, and were agitated in the liquor using a polyethylene spatula. After exactly 10 minutes, the test specimens were removed from the liquor, fixed to a line to dry, and not measured until the following day.

Testing of Hydrophilicity:

To verify the hydrophilicity, a test method based on DIN 53924 was used to measure the wicking of water. These measurements were always carried out relative to a comparative sample, and for this reason a conditioned environment was not employed. Comparison always took place only within one measurement series. The treated test fabric was cut in each case into five strips 25 cm long and 1.5 cm wide, marked at the side with a water-soluble pen, and fastened tightly but without tension, vertically, on a mount. The mount was then placed in a water tank for five minutes in such a way that 2 cm of the strip was immersed in the water. The purpose of the water-soluble marking is to facilitate the recognisability of the wicking height, by the running of the ink when wetted with water. When the mount has stood outside the water tank for 10 minutes, the wicking height is read off in cm and determined against the blank value (wicking height of the untreated cotton strips×cm=100%), and expressed as a % of the blank value.

The results are reported in the two tables below.

Determination of the Wicking Height on Woven Cotton Goods.

| Composition | Wicking height as % of blank value |
| --- | --- |
| Comparative example Rewoquat ® WE-18 | 63.0 |
| Synthesis Example S8 | 86.0 |
| Synthesis Example S8 + Rewoquat ® WE-18 (20:80) | 72.0 |
| Synthesis Example S6-182 | 88.0 |
| Synthesis Example S6-182 + Rewoquat ® WE-18 (20:80) | 71.0 |
| Untreated | 100.0 |

On application to a cotton textile, a significantly increased hydrophilicity of the fibre is found, relative to the comparative example. Even low levels of addition, of only 20% of the total amount of active ingredient, also produce a significant reduction in the hydrophobization caused by the softener ingredient. Both of these facts are especially surprising since the skilled person knows siloxanes to be highly hydrophobizing.

Determination of the Wicking Height on Polyester Fabric

| Composition | Wicking height as % of blank value |
| --- | --- |
| Comparative example Rewoquat ® WE-18 | 65.0 |
| Synthesis Example S8 | 97.0 |
| Synthesis Example S8 + Rewoquat ® WE-18 (20:80) | 95.0 |
| Synthesis Example S6 | 90.0 |
| Synthesis Example S6 + Rewoquat ® WE-18 (20:80) | 88.0 |
| Untreated | 100.0 |

It has also been found that on application to polyester fabric the result is a significantly increased hydrophilicity of the fibre relative to the comparative example, almost to the point of the blank value. Even low levels of addition, of only 20% of the total amount of active ingredient, also produce a significant reduction in the hydrophobization caused by the softener ingredient. Both of these facts are especially surprising since the skilled person knows siloxanes to be highly hydrophobizing.

Haircare Examples:

1. Testing of the Conditioning of Hair by Means of Sensory Tests in a Hair Rinse:

For performance assessment in the conditioning of hair, the compounds of the present invention from Synthesis Examples S8, S6 and S5 were used, along with the commercially available product ABIL® Quat 3272 (INCI: Quaternium-80, manufacturer: Evonik Industries), in a simple cosmetic hair rinse formulation.

The performance properties on use in hair rinses were verified in the following formulations:

| | Formulation Examples | | | | |
|---|---|---|---|---|---|
| | 0a | 1a | 2a | 3a | V4a |
| TEGINACID ® C, Evonik Industries (INCI: Ceteareth-25) | 0.5% | 0.5% | 0.5% | 0.5% | 0.5% |
| TEGO ® Alkanol 16, Evonik Industries (INCI: Cetyl alcohol) | 5.0% | 5.0% | 5.0% | 5.0% | 5.0% |
| VARISOFT ® 300, 30% strength, Evonik Industries (INCI: Cetrimonium chloride (=CTAC)) | 2.0% | 2.0% | 2.0% | 2.0% | 2.0% |
| Neolone PE, The Dow Chemical Company (INCI: Phenoxyethanol; methylisothiazolinone) | 0.45% | 0.45% | 0.45% | 0.45% | 0.45% |
| Water, demineralized | Ad 100.0% | | | | |
| Citric acid | ad pH 4.5 ± 0.3 | | | | |
| Synthesis Example S8, 80% strength in isopropanol (inventive) | | 0.38% | | | |
| Synthesis Example S6, 80% strength in isopropanol (inventive) | | | 0.38% | | |
| Synthesis Example S5, 80% strength in isopropanol (inventive) | | | | 0.38% | |
| ABIL ® Quat 3272, 50% strength in propylene glycol (not inventive) | | | | | 0.60% |

For the performance assessment, hair tresses which are used for sensory tests were subjected to standardized predamaging by means of a bleaching treatment. For this, customary hairstyling products were used. The test procedure, the base materials used, and the details of the assessment criteria have been described in DE 103 27 871.

The hair was pretreated using a shampoo which contained no conditioners.

Standardized Treatment of Predamaged Hair Tresses with Conditioning Formulations:

The hair tresses predamaged as described above were treated as follows with the above-described conditioning rinse:

The hair tresses were wetted under running warm water. The excess water was pressed out gently by hand, and then the shampoo was applied and worked gently into the hair (1 ml/tress (2 g)). After a contact time of 1 min, the hair was rinsed for 1 min Immediately afterwards, the rinse was applied and was worked gently into the hair (1 ml/tress (2 g)). After a contact time of 1 min, the hair was rinsed for 1 min Assessment Criteria:

The sensory evaluations were made according to grades awarded on a scale from 1 to 5, with 1 being the worst and 5 the best evaluation. The individual test criteria were each given their own evaluation.

The test criteria were as follows: Wet combability, wet feel, dry combability, dry feel, appearance/shine.

The table below compares the results of the sensory assessment of the treatment, carried out as described above, on the hair tresses with the inventive formulations 1a, 2a and 3a, with the comparative formulation V4a and with the control formulation 0a (placebo without test substance).

| | Wet combability | Wet feel | Dry combability | Dry feel | Shine |
|---|---|---|---|---|---|
| Control formulation 0a | 3.9 | 4.0 | 4.1 | 4.5 | 3.0 |
| Inventive formulation 1a | 4.5 | 4.1 | 4.3 | 4.4 | 4.0 |
| Inventive formulation 2a | 4.9 | 4.4 | 4.5 | 4.7 | 4.5 |
| Inventive formulation 3a | 4.9 | 4.5 | 4.8 | 4.8 | 4.5 |
| Comparative formulation (not inventive) V4a | 4.7 | 4.3 | 4.6 | 4.8 | 3.5 |

The inventive formulations 1a, 2a and 3a with the inventive compounds from Synthesis Examples S8, S6 and S5 exhibited good cosmetic evaluations in the sensory assessment. The control formulation 0a (with CTAC) was improved significantly by the addition of only 0.3% of silicone product on an active basis. The already very good properties of the comparative formulation V4a with respect to wet combability and wet feel were increased still further here by the inventive formulations 2a and 3a with the inventive compounds of Examples 2 and 3. A significantly better evaluation was also achieved for the shine through the use of the inventive formulations 1a, 2a and 3a.

2.) Testing of the Conditioning of Hair by Means of Sensory Tests from a Shampoo:

In addition to the abovementioned hair rinse formulation, the conditioning of hair was assessed on a performance basis using the inventive compounds from Synthesis Examples S8, S6 and S5 and also the commercially available product ABIL® Quat 3272 (INCI: Quaternium-80, manufacturer: Evonik Industries) in a simple cosmetic shampoo formulation as well.

The performance properties on use in shampoos was verified in the following formulas:

|  | Formulation Examples | | | | |
| --- | --- | --- | --- | --- | --- |
|  | 0b | 1b | 2b | 3b | V4b |
| Texapon NSO-IS, 28% strength, BASF (INCI: Sodium Laureth Sulphate) | 32.0% | 32.0% | 32.0% | 32.0% | 32.0% |
| TEGO ® Betain F 50, 38% strength, Evonik Industries (INCI: Cocamidopropyl betaine) | 8.0% | 8.0% | 8.0% | 8.0% | 8.0% |
| Polymer JR 400, Amerchol (INCI: Polyquaternium-10 (=PQ-10)) | 0.2% | 0.2% | 0.2% | 0.2% | 0.2% |
| ANTIL ® 171, Evonik Industries (INCI: PEG-18 Glyceryl Oleate/Cocoate) | 2.5% | 2.5% | 2.5% | 2.5% | 2.5% |
| NaCl | 0.5% | 0.5% | 0.5% | 0.5% | 0.5% |
| Neolone PE, The Dow Chemical Company (INCI: Phenoxyethanol; Methylisothiazolinone)) | 0.45% | 0.45% | 0.45% | 0.45% | 0.45% |
| Water, demineralized | Ad 100.0% | | | | |
| Citric acid | ad pH 5.5 ± 0.3 | | | | |
| Synthesis Example S8, 80% strength in isopropanol (inventive) |  | 1.25% |  |  |  |
| Synthesis Example S6, 80% strength in isopropanol (inventive) |  |  | 1.25% |  |  |
| Synthesis Example S5, 80% strength in isopropanol (inventive) |  |  |  | 1.25% |  |
| ABIL ® Quat 3272, 50% strength in propylene glycol (not inventive) |  |  |  |  | 2.0% |
| Viscosity [mPa · s] | 3700 | 290 | 420 | 6000 | 150 |

Surprisingly, even the Product Examples 2 and 3, with a long silicone chain, form clear solutions in this shampoo formulation.

It is surprising, moreover, that the inventive products do not lead to such a great reduction in the viscosities in this shampoo formulation as does the comparative product. Particularly surprising is the fact that the compound from Synthesis Example S5 in fact shows an increase in the viscosity. This effect is highly relevant to formulators, since the use of thickeners can be reduced.

For the performance assessment, hair tresses were subjected to predamaging as described above under 1). The treatment with the conditioning shampoo formulations likewise took place in accordance with the method described above. Instead of the hair rinse, however, the shampoo formulations were employed.

The table below compares the results of the sensory assessment of the treatment, carried out as described above, of the hair tresses with the inventive formulations 1b, 2b and 3b, with the comparative formulation V4b and with the control formulation 0b (placebo without test substance).

|  | Wet combability | Wet feel | Dry combability | Dry feel | Shine |
| --- | --- | --- | --- | --- | --- |
| Control formulation 0b | 2.9 | 2.9 | 3.9 | 4.1 | 3.0 |
| Inventive formulation 1b | 4.3 | 4.0 | 4.0 | 4.0 | 4.0 |
| Inventive formulation 2b | 4.4 | 4.1 | 4.7 | 4.5 | 4.5 |
| Inventive formulation 3b | 4.1 | 4.5 | 4.8 | 4.8 | 4.0 |
| Comparative formulation (not inventive) V4b | 4.0 | 3.8 | 4.1 | 4.4 | 3.5 |

The inventive formulations 1b, 2b and 3b with the inventive compounds from Synthesis Examples S8, S6 and S5 show very good cosmetic evaluations in the sensory assessment. The control formulation 0b (with PQ-10) was improved significantly by the addition of silicone products. The inventive formulations 2b and 3b especially, with the inventive compounds from Synthesis Examples S6 and S5, consistently showed values which were in fact very much better than those of comparative formulation V4b, which is already good. Especially surprising here are the extremely good values for dry combability and dry feel, since on dry hair, any differentiation is normally difficult. In the case of wet combability and wet feel, the inventive formulation 1b, with the inventive compound of Example 1, was also significantly better than the comparative formulation V4b.

In the case of shine as well, the superiority of the inventive formulations 1b, 2b and 3b was evident.

FURTHER FORMULATION EXAMPLES

The formulation examples given in the tables below show exemplary representatives of a large number of possible compositions according to the present invention.

If the preparation of the formulation requires the separate preparation or mixing of formulation constituents beforehand, this is termed multiphase preparation.

If a two-phase preparation is required, the two phases are labelled A and B in the stated tables. In the case of three-phase processes, the three phases are called A, B and C. Unless otherwise indicated, the amounts in the tables below are amounts in weight %.

Formulation Example 1

Clear Shampoo

| | |
|---|---|
| TEXAPON ® NSO, BASF, 28% strength (INCI: Sodium Laureth Sulphate) | 32.00% |
| Synthesis Example S8 | 2.50% |
| Perfume | 0.50% |
| Water | 55.50% |
| TEGO ® Betain F 50, Evonik Industries, 38% strength (INCI: Cocamidopropyl Betaine) | 8.00% |
| ANTIL ® 171, Evonik Industries (INCI: PEG-18 Glyceryl Oleate/Cocoate) | 1.00% |
| NaCl | 0.50% |
| Preservative | q.s. |

Formulation Example 2

Shampoo, PEG- & Sulphate-Free

| | |
|---|---|
| REWOTERIC ® AM C, Evonik Industries, 32% strength (INCI: Sodium Cocoamphoacetate) | 15.00% |
| Plantapon ACG 50, BASF (INCI: Disodium Cocoyl Glutamate) | 3.80% |
| Synthesis Example S6 | 2.00% |
| Perfume | 0.30% |
| Water | 64.30% |
| TEGO ® Betain F 50, Evonik Industries, 38% strength (INCI: Cocamidopropyl Betaine) | 10.00% |
| VARISOFT ® PATC, Evonik Industries (INCI: Palmitamidopropyltrimonium Chloride) | 2.30% |
| ANTIL ® SPA 80, Evonik Industries (INCI: Isostearamide MIPA; Glyceryl Laurate) | 2.00% |
| Preservative | 0.30% |
| Citric acid, 30% strength | q.s. |

Formulation Example 3

Clear Conditioning Shampoo

| | |
|---|---|
| TEXAPON ® NSO, BASF, 28% strength (INCI: Sodium Laureth Sulphate) | 32.00% |
| ANTIL ® 200, Evonik Industries (INCI: PEG-200 Hydrogenated Glyceryl Palmate; PEG-7 Glyceryl Cocoate) | 2.00% |
| Synthesis Example S5 | 2.00% |
| Perfume | 0.25% |
| Water | 55.25% |
| Polymer JR 400, Amerchol (INCI: Polyquaternium-10) | 0.20% |
| TEGO ® Betain F 50, Evonik Industries, 38% strength (INCI: Cocamidopropyl Betaine) | 8.00% |
| NaCl | 0.30% |
| Preservative | q.s. |

Formulation Example 4

Clear Conditioning Shampoo

| | |
|---|---|
| TEXAPON ® NSO, BASF, 28% strength (INCI: Sodium Laureth Sulphate) | 32.00% |
| ANTIL ® 200, Evonik Industries (INCI: PEG-200 Hydrogenated Glyceryl Palmate; PEG-7 Glyceryl Cocoate) | 2.00% |
| ABIL ® Quat 3272, Evonik Industries (INCI: Quaternium-80) | 0.75% |
| Synthesis Example S8 | 1.50% |
| Perfume | 0.25% |
| Water | 55.00% |
| Polymer JR 400, Amerchol (INCI: Polyquaternium-10) | 0.20% |
| TEGO ® Betain F 50, Evonik Industries, 38% strength (INCI: Cocamidopropyl Betaine) | 8.00% |
| NaCl | 0.30% |
| Preservative | q.s. |

Formulation Example 5

Clear Conditioning Shampoo

| | |
|---|---|
| TEXAPON ® NSO, BASF, 28% strength (INCI: Sodium Laureth Sulphate) | 32.00% |
| ANTIL ® 200, Evonik Industries (INCI: PEG-200 Hydrogenated Glyceryl Palmate; PEG-7 Glyceryl Cocoate) | 2.00% |
| ABIL ® B 8832, Evonik Industries (INCI: Bis-PEG/PPG-20/20 Dimethicone) | 0.50% |
| Synthesis Example S6 | 3.50% |
| Perfume | 0.25% |
| Water | 53.25% |
| Polymer JR 400, Amerchol (INCI: Polyquaternium-10) | 0.20% |
| TEGO ® Betain F 50, Evonik Industries, 38% strength (INCI: Cocamidopropyl Betaine) | 8.00% |
| NaCl | 0.30% |
| Preservative | q.s. |

Formulation Example 6

Clear Conditioning Shampoo

| | |
|---|---|
| TEXAPON ® NSO, BASF, 28% strength (INCI: Sodium Laureth Sulphate) | 32.00% |
| VARISOFT ® PATC, Evonik Industries (INCI: Palmitamidopropyltrimonium Chloride) | 1.50% |
| REWODERM ® LI S 80, Evonik Industries (INCI: PEG-200 Hydrogenated Glyceryl Palmate; PEG-7 Glyceryl Cocoate) | 2.00% |
| Synthesis Example S8 | 2.50% |
| Perfume | 0.25% |
| Water | 52.05% |
| TEGO ® Cosmo C 100, Evonik Industries (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Industries, 38% strength (INCI: Cocamidopropyl Betaine) | 8.00% |
| NaCl | 0.50% |
| Preservative | q.s. |

Formulation Example 7

Clear Conditioning Shampoo

| | |
|---|---|
| TEXAPON ® NSO, BASF, 28% strength (INCI: Sodium Laureth Sulphate) | 32.00% |

| | |
|---|---|
| REWODERM ® LI S 80, Evonik Industries (INCI: PEG-200 Hydrogenated Glyceryl Palmate; PEG-7 Glyceryl Cocoate) | 2.00% |
| Synthesis Example S6 | 2.50% |
| Perfume | 0.25% |
| Water | 53.55% |
| TEGO ® Cosmo C 100, Evonik Industries (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Industries, 38% strength (INCI: Cocamidopropyl Betaine) | 8.00% |
| NaCl | 0.50% |
| Preservative | q.s. |

Formulation Example 8

Pearlized Shampoo

| | |
|---|---|
| TEXAPON ® NSO, BASF, 28% strength (INCI: Sodium Laureth Sulphate) | 32.00% |
| Synthesis Example S8 | 5.50% |
| Perfume | 0.25% |
| Water | 49.25% |
| TEGO ® Betain F 50, Evonik Industries, 38% strength (INCI: Cocamidopropyl Betaine) | 8.00% |
| TEGO ® Pearl N 300 Evonik Industries (INCI: Glycol Distearate; Laureth-4; Cocamidopropyl Betaine) | 2.00% |
| ANTIL ® 171 Evonik Industries (INCI: PEG-18 Glyceryl Oleate/Cocoate) | 2.50% |
| NaCl | 0.50% |
| Preservative | q.s. |

Formulation Example 9

Shampoo, PEG- & Sulphate-Free

| | | |
|---|---|---|
| A | REWOTERIC ® AM C, Evonik Industries, 32% strength (INCI: Sodium Cocoamphoacetate) | 20.00% |
| | REWOPOL ® SB F 12 P, Evonik Goldschmidt, 96% strength (INCI: Disodium Lauryl Sulphosuccinate) | 5.90% |
| | Synthesis Example S6 | 2.00% |
| | ANTIL ® SPA 80, Evonik Industries, (INCI: Isostearamide MIPA; Glyceryl Laurate) | 1.70% |
| B | Water | 63.20% |
| | Citric acid, 30% strength | 3.60% |
| C | ANTIL ® HS 60, Evonik Industries, (INCI: Cocamidopropyl Betaine; Glyceryl Laurate) | 3.00% |
| | Preservative | 0.60% |

Formulation Example 10

Rinse-Off Conditioner

| | |
|---|---|
| Water | 85.50% |
| VARISOFT ® BT 85, Evonik Industries (INCI: Behentrimonium chloride) | 3.00% |
| Synthesis Example S6 | 5.50% |
| TEGO ® Alkanol 1618, Evonik Industries (INCI: Cetearyl alcohol) | 5.00% |
| Preservative, perfume | q.s. |

Formulation Example 11

Rinse-Off Conditioner

| | |
|---|---|
| Water | 90.20% |
| VARISOFT ® EQ 65, Evonik Industries (INCI: Distearoylethyl Dimonium Chloride; Cetearyl Alcohol) | 2.00% |
| VARISOFT ® BT 85, Evonik Industries (INCI: Behentrimonium Chloride) | 1.00% |
| Synthesis Example S8 | 1.80% |
| TEGO ® Alkanol 1618, Evonik Industries (INCI: Cetearyl Alcohol) | 5.00% |
| Preservative, perfume | q.s. |

Formulation Example 12

Rinse-Off Conditioner

| | |
|---|---|
| Water | 87.20% |
| VARISOFT ® EQ 65, Evonik Industries (INCI: Distearoylethyl Dimonium Chloride; Cetearyl Alcohol) | 2.00% |
| VARISOFT ® BT 85, Evonik Industries (INCI: Behentrimonium Chloride) | 2.00% |
| ABIL ® Quat 3272, Evonik Industries (INCI: Quaternium-80) | 0.50% |
| Synthesis Example S8 | 3.30% |
| TEGO ® Alkanol 1618, Evonik Industries (INCI: Cetearyl Alcohol) | 5.00% |
| Preservative, perfume | q.s. |

Formulation Example 13

Rinse-Off Conditioner

| | |
|---|---|
| TEGINACID ® C, Evonik Industries (INCI: Ceteareth-25) | 0.50% |
| TEGO ® Alkanol 16, Evonik Industries (INCI: Cetyl Alcohol) | 2.00% |
| TEGO ® Amid S 18, Evonik Industries (INCI: Stearamidopropyl Dimethylamine) | 1.00% |
| Synthesis Example S6 | 5.50% |
| Propylene Glycol | 2.00% |
| Citric Acid Monohydrate | 0.30% |
| Water | 88.70% |
| Preservative, perfume | q.s. |

Formulation Example 14

Rinse-Off Conditioner

| | |
|---|---|
| TEGINACID ® C, Evonik Industries (INCI: Ceteareth-25) | 0.50% |
| TEGO ® Alkanol 16, Evonik Industries (INCI: Cetyl Alcohol) | 5.00% |

-continued

| | |
|---|---|
| TEGOSOFT ® DEC, Evonik Industries (INCI: Diethylhexyl Carbonate) | 1.00% |
| Synthesis Example S6 | 3.50% |
| Water | 87.20% |
| TEGO ® Cosmo C 100 Evonik Industries (INCI: Creatine) | 0.50% |
| Propylene Glycol | 2.00% |
| Citric Acid Monohydrate | 0.30% |
| Preservative, perfume | q.s. |

Formulation Example 15

Leave-in Conditioner Spray

| | |
|---|---|
| Lactic Acid, 80% | 0.40% |
| Water | 92.30% |
| TEGO ® Amid S 18, Evonik Industries (INCI: Stearamidopropyl Dimethylamine) | 1.20% |
| TEGIN ® G 1100 Pellets, Evonik Industries (INCI: Glycol Distearate) | 0.60% |
| TEGO ® Care PS, Evonik Industries (INCI: Methyl Glucose Sesquistearate) | 1.20% |
| TEGOSOFT ® DEC, Evonik Industries (INCI: Diethylhexyl Carbonate) | 0.30% |
| Synthesis Example S8 | 4.00% |
| Preservative, perfume | q.s. |

Formulation Example 16

Leave-in Conditioner Spray

| | |
|---|---|
| TAGAT ® CH 40, Evonik Industries (INCI: PEG-40 Hydrogenated Castor Oil) | 2.00% |
| Ceramide VI, Evonik Industries (INCI: Ceramide 6 II) | 0.05% |
| Perfume | 0.20% |
| Water | 81.95% |
| Synthesis Example S6 | 9.50% |
| LACTIL ®, Evonik Industries (INCI: Sodium Lactate; Sodium PCA; Glycine; Fructose; Urea; Niacinamide; Inositol; Sodium benzoate; Lactic Acid) | 2.00% |
| TEGO ® Betain F 50, Evonik Industries 38% (INCI: Cocamidopropyl betaine) | 2.30% |
| Citric acid (10% in water) | 2.00% |

Formulation Example 17

Leave-in Conditioner Foam

| | |
|---|---|
| Synthesis Example S6 | 3.50% |
| TAGAT ® CH 40, Evonik Industries (INCI: PEG-40 Hydrogenated Castor Oil) | 0.50% |
| Perfume | 0.30% |
| TEGO ® Betain 810, Evonik Industries (INCI: Capryl/Capramidopropyl Betaine) | 2.00% |
| Water | 91.00% |
| TEGO ® Cosmo C 100, Evonik Industries (INCI: Creatine) | 0.50% |
| TEGOCEL ® HPM 50, Evonik Industries (INCI: Hydroxypropyl Methylcellulose) | 0.30% |
| VARISOFT ® 300, Evonik Industries (INCI: Cetrimonium Chloride) | 1.30% |
| LACTIL ® Evonik Industries (INCI: Sodium Lactate; Sodium PCA; Glycine; Fructose; Urea; Niacinamide; Inositol; Sodium benzoate; Lactic Acid) | 0.50% |

-continued

| | |
|---|---|
| Citric acid (30% in water) | 0.10% |
| Preservative | q.s. |

Formulation Example 18

Strong Hold Styling Gel

| | |
|---|---|
| TEGO ® Carbomer 141, Evonik Industries (INCI: Carbomer) | 1.20% |
| Water | 65.00% |
| NaOH, 25% | 2.70% |
| PVP/VA W-735, ISP (INCI: PVP/VA Copolymer) | 16.00% |
| Synthesis Example S8 | 2.50% |
| Alcohol denate. | 10.00% |
| TAGAT ® O 2 V, Evonik Industries (INCI: PEG-20 Glyceryl Oleate) | 2.00% |
| Perfume | 0.30% |
| ABIL ® B 88183, Evonik Industries (INCI: PEG/PPG-20/6 Dimethicone) | 0.30% |
| Preservative | q.s. |

Formulation Example 19

Bodycare Foam

| | |
|---|---|
| TEXAPON ® NSO, BASF, 28% strength (INCI: Sodium Laureth Sulphate) | 14.30% |
| Perfume | 0.30% |
| Synthesis Example S6 | 1.50% |
| REWOTERIC ® AM C, Evonik Industries, 32% strength (INCI: Sodium Cocoamphoacetate) | 8.00% |
| Water | 73.90% |
| TEGOCEL ® HPM 50, Evonik Industries (INCI: Hydroxypropyl Methylcellulose) | 0.50% |
| LACTIL ®, Evonik Industries (INCI: Sodium Lactate; Sodium PCA; Glycine; Fructose; Urea; Niacinamide; Inositol; Sodium benzoate; Lactic Acid) | 1.00% |
| Citric Acid Monohydrate | 0.50% |

Formulation Example 20

Bodycare Product

| | |
|---|---|
| TEXAPON ® NSO, BASF, 28% strength (INCI: Sodium Laureth Sulphate) | 30.00% |
| TEGOSOFT ® PC 31, Evonik Industries (INCI: Polyglyceryl-3 Caprate) | 0.50% |
| Synthesis Example S8 | 1.50% |
| Perfume | 0.30% |
| Water | 52.90% |
| TEGOCEL ® HPM 4000, Evonik Industries (INCI: Hydroxypropyl methylcellulose) | 0.30% |
| REWOTERIC ® AM C, Evonik Industries, 32% strength (INCI: Sodium Cocoamphoacetate) | 10.00% |
| Citric Acid Monohydrate | 0.50% |
| REWODERM ® LI S 80, Evonik Industries (INCI: PEG-200 Hydrogenated Glyceryl Palmate; PEG-7 Glyceryl Cocoate) | 2.00% |
| TEGO ® Pearl N 300, Evonik Industries (INCI: Glycol Distearate; Laureth-4; Cocamidopropyl Betaine) | 2.00% |

Formulation Example 21

Bodycare Foam

| | |
|---|---|
| TEXAPON ® NSO, BASF, 28% strength | 14.30% |
| (INCI: Sodium Laureth Sulphate) | |
| Perfume | 0.30% |
| Synthesis Example S6 | 1.00% |
| REWOTERIC ® AM C, Evonik Industries, 32% strength | 8.00% |
| (INCI: Sodium Cocoamphoacetate) | |
| Water | 75.10% |
| Polyquaternium-7, Nalco, (INCI: Merquat 550) | 0.30% |
| LACTIL ®, Evonik Industries | 0.50% |
| (INCI: Sodium Lactate; Sodium PCA; Glycine; Fructose; Urea; Niacinamide; Inositol; Sodium benzoate; Lactic Acid) | |
| Citric Acid Monohydrate | 0.50% |

Formulation Example 22

Mild Foam Bath

| | |
|---|---|
| TEXAPON ® NSO, BASF, 28% strength | 27.00% |
| (INCI: Sodium Laureth Sulphate) | |
| REWOPOL ® SB FA 30, Evonik Industries, 40% strength | 12.00% |
| (INCI: Disodium Laureth Sulphosuccinate) | |
| TEGOSOFT ® LSE 65 K SOFT, Evonik Industries | 2.00% |
| (INCI: Sucrose Cocoate) | |
| Water | 38.00% |
| REWOTERIC ® AM C, Evonik Industries, 32% strength | 13.00% |
| (INCI: Sodium Cocoamphoacetate) | |
| Synthesis Example S8 | 1.50% |
| Citric acid (30% in water) | 3.00% |
| ANTIL ® 171, Evonik Industries | 1.50% |
| (INCI: PEG-18 Glyceryl Oleate/Cocoate) | |
| TEGO ® Pearl N 300 Evonik Industries | 2.00% |
| (INCI: Glycol Distearate; Laureth-4; Cocamidopropyl Betaine) | |

Formulation Example 23

Rinse-Off Conditioner

| | |
|---|---|
| Water | 88.20% |
| VARISOFT ® 300, Evonik Industries | 2.00% |
| (INCI: Cetrimonium Chloride) | |
| VARISOFT ® BT 85, Evonik Industries | 2.00% |
| (INCI: Behentrimonium Chloride) | |
| ABIL ® OSW 5, Evonik Industries | 1.00% |
| (INCI: Cyclopentasiloxane; Dimethiconol) | |
| Synthesis Example S6 | 1.80% |
| TEGO ® Alkanol 1618, Evonik Industries | 5.00% |
| (INCI: Cetearyl Alcohol) | |
| Preservative, perfume | q.s. |

Formulation Example 24

Rinse-Off Conditioner

| | |
|---|---|
| Water | 87.20% |
| VARISOFT ® EQ 65, Evonik Industries | 2.00% |
| (INCI: Distearoylethyl Dimonium Chloride; Cetearyl Alcohol) | |
| VARISOFT ® BT 85, Evonik Industries | 2.00% |
| (INCI: Behentrimonium Chloride) | |
| ABIL ® Soft AF 100, Evonik Industries | 1.00% |
| (INCI: Methoxy PEG/PPG-7/3 Aminopropyl Dimethicone) | |
| Synthesis Example S8 | 2.80% |
| TEGO ® Alkanol 1618, Evonik Industries | 5.00% |
| (INCI: Cetearyl Alcohol) | |
| Preservative, perfume | q.s. |

Formulation Example 25

Rinse-Off Conditioner

| | |
|---|---|
| Water | 88.20% |
| VARISOFT ® BT 85, Evonik Industries | 3.00% |
| (INCI: Behentrimonium Chloride) | |
| SF 1708, Momentive | 2.00% |
| (INCI: Amodimethicone) | |
| Synthesis Example S6 | 1.80% |
| TEGO ® Alkanol 1618, Evonik Industries | 5.00% |
| (INCI: Cetearyl Alcohol) | |
| Preservative, perfume | q.s. |

Formulation Example 26

Moisturizing Skin Cleanser

| | | | |
|---|---|---|---|
| A | TEXAPON ® NSO, BASF, 28% strength | | 30.00% |
| | (INCI: Sodium Laureth Sulphate) | | |
| | Synthesis Example S8 | | 1.70% |
| | Perfume | | 0.30% |
| B | Water | | 54.60% |
| | TEGOCEL ® fluid HPM 4000, Evonik Industries | | 1.20% |
| | (INCI: Hydroxypropyl Methylcellulose) | | |
| | TEGO ® Betain C 60, Evonik Industries, 46% strength | | 8.10% |
| | (INCI: Cocamidopropyl Betaine) | | |
| | TEGOSOFT ® APM, Evonik Industries | | 1.00% |
| | (INCI: PPG-3 Myristyl Ether) | | |
| | Cutina TS, BASF (INCI: PEG-3 Distearate) | | 1.00% |
| | REWODERM ® LI S 80, Evonik Industries | | 1.50% |
| | (INCI: PEG-200 Hydrogenated Glyceryl Palmate; PEG-7 Glyceryl Cocoate) | | |
| | Preservative | | 0.60% |
| | Citric acid, 30% strength | | q.s. |

Formulation Example 27

Shower Gel

| | |
|---|---|
| TEXAPON ® NSO, BASF, 28% strength | 15.00% |
| (INCI: Sodium Laureth Sulphate) | |
| Synthesis Example S6 | 1.50% |
| Perfume | 0.30% |
| PGFAC-S, BASF | 1.50% |
| (INCI: Sodium Cocoyl Hydrolyzed Wheat Protein Glutamate) | |
| REWOPOL ® SB CS 50 B, Evonik Industries, 40% strength | 7.50% |
| (INCI: Disodium PEG-5 Laurylcitrate Sulphosuccinate; Sodium Laureth Sulphate) | |
| Water | 58.10% |
| TEGO ® Betain F 50, Evonik Industries, 38% strength | 9.00% |
| (INCI: Cocamidopropyl Betaine) | |

| | | |
|---|---|---|
| TEGO ® Betain 810, Evonik Industries, 38% strength (INCI: Capryl/Capramidopropyl Betaine) | | 4.00% |
| Polyquaternium-7, Nalco, (INCI: Merquat 550) | | 0.50% |
| ANTIL ® 200, Evonik Industries, (INCI: PEG-200 Hydrogenated Glyceryl Palmate; PEG-7 Glyceryl Cocoate) | | 2.30% |
| Preservative | | 0.30% |

Formulation Example 28

Body Cleanser

| | | |
|---|---|---|
| A | TEXAPON ® NSO BASF 28% strength (INCI: Sodium Laureth Sulphate) | 30.00% |
| | Synthesis Example S8 | 1.50% |
| | ABIL ® B 8832, Evonik Industries (INCI: Bis-PEG/PPG-20/20 Dimethicone) | 0.30% |
| | Perfume | 0.30% |
| B | Water | 51.00% |
| | TEGOCEL ® fluid HPM 4000, Evonik Industries (INCI: Hydroxypropyl Methylcellulose) | 1.20% |
| | Citric Acid Monohydrate | 0.50% |
| | REWOTERIC ® AM C, Evonik Industries, 32% strength (INCI: Sodium Cocoamphoacetate) | 10.00% |
| | Cutina TS, BASF (INCI: PEG-3 Distearate) | 2.00% |
| | REWODERM ® LI S 80, Evonik Industries (INCI: PEG-200 Hydrogenated Glyceryl Palmate; PEG-7 Glyceryl Cocoate) | 2.60% |
| | Preservative | 0.60% |
| | Citric acid, 30% strength | q.s. |

Formulation Example 29

Body Cleansing Foam

| | |
|---|---|
| TEXAPON ® NSO, BASF, 28% strength (INCI: Sodium Laureth Sulphate) | 14.00% |
| Perfume | 0.30% |
| Synthesis Example S6 | 0.70% |
| REWOTERIC ® AM C, Evonik Industries, 32% strength (INCI: Sodium Cocoamphoacetate) | 8.00% |
| Water | 74.80% |
| TEGOCEL ® HPM 50, Evonik Industries (INCI: Hydroxypropyl Methylcellulose) | 0.50% |
| LACTIL ®, Evonik Industries (INCI: Sodium Lactate; Sodium PCA; Glycine; Fructose; Urea; Niacinamide; Inositol; Sodium Benzoate; Lactic Acid) | 1.00% |
| Panthenol, BASF (INCI: D-Panthenol USP) | 0.20% |
| Citric Acid Monohydrate | 0.50% |

Formulation Example 30

Turbid Conditioning Shampoo

| | |
|---|---|
| TEXAPON ® NSO, BASF, 28% strength (INCI: Sodium Laureth Sulphate) | 32.00% |
| ANTIL ® 200, Evonik Industries (INCI: PEG-200 Hydrogenated Glyceryl Palmate; PEG-7 Glyceryl Cocoate) | 2.00% |
| Synthesis Example S8 | 1.00% |
| Perfume | 0.25% |
| Water | 53.25% |
| Polymer JR 400, Amerchol (INCI: Polyquaternium-10) | 0.20% |
| TEGO ® Betain F 50, Evonik Industries, 38% strength (INCI: Cocamidopropyl Betaine) | 8.00% |
| DC1503 Fluid, Dow Corning (INCI: Dimethicone; Dimethiconol) | 1.00% |
| TEGO ® Pearl N 300 Evonik Industries (INCI: Glycol Distearate; Laureth-4; Cocamidopropyl Betaine) | 2.00% |
| NaCl | 0.30% |
| Preservative | q.s. |

Formulation Example 31

Mild Hair & Body Wash, PEG- and Sulphate-Free

| | |
|---|---|
| Plantacare ® 1200 UP, BASF, 50% strength (INCI: Lauryl Glucoside) | 11.40% |
| Plantacare ® 818 UP, BASF, 51% strength (INCI: Coco Glucoside) | 5.60% |
| Water | 61.60% |
| ANTIL ® SOFT SC, Evonik Industries (INCI: Sorbitan Sesquicaprylate) | 0.90% |
| Synthesis Example S6 | 1.00% |
| TEGOSOFT ® LSE 65 K SOFT, Evonik Industries (INCI: Sucrose Cocoate) | 1.50% |
| TEGO ® Betain F 50, Evonik Industries, 38% strength (INCI: Cocamidopropyl Betaine) | 18.00% |
| Perfume, preservative | q.s. |
| Citric Acid, 30% | q.s. |

Formulation Example 32

Sprayable Hairmilk, PEG-Free

| | | |
|---|---|---|
| A | Water | 95.30% |
| | Lactic acid, 80% strength | 0.40% |
| B | TEGO ® AMID S 18, Evonik Industries (INCI: Stearamidopropyl Dimethylamine) | 1.20% |
| | TEGIN ® G 1100 Pellets, Evonik Industries (INCI: Glycol Distearate) | 0.60% |
| | TEGO ® Care PS, Evonik Industries (INCI: Methyl Glucose Sesquistearate) | 1.20% |
| | TEGOSOFT ® DEC, Evonik Industries (INCI: Diethylhexyl Carbonate) | 0.30% |
| | Synthesis Example S6 | 1.00% |
| | Perfume, preservative | q.s. |

Formulation Example 33

Pearlized Shampoo

| | |
|---|---|
| TEXAPON ® NSO, Cognis, 28% strength (INCI: Sodium Laureth Sulphate) | 32.00% |
| Synthesis Example S8 | 0.75% |
| Perfume | 0.25% |
| Water | 56.00% |
| TEGO ® Betain F 50, Evonik Industries, 38% strength (INCI: Cocamidopropyl Betaine) | 8.00% |
| TEGIN ® D 1102, Evonik Industries (INCI: PEG-3 Distearate) | 1.00% |
| ANTIL ® 171, Evonik Industries (INCI: PEG-18 Glyceryl Oleate/Cocoate) | 1.50% |
| NaCl | 0.50% |
| Preservative | q.s. |

Formulation Example 34

"Two in One" Shampoo

| | | |
|---|---|---|
| A | TEXAPON ® NSO, Cognis, 28% strength (INCI: Sodium Laureth Sulphate) | 30.00% |
| | Perfume | 0.50% |
| | Stepanate ® SCS, Stepan (INCI: Sodium Cumenesulphonate) | 1.00% |
| | Water | 16.25% |
| | TEGO ® Betain F 50, Evonik Industries, 38% strength (INCI: Cocamidopropyl Betaine) | 8.00% |
| B | TEXAPON ® NSO, Cognis, 28% strength (INCI: Sodium Laureth Sulphate) | 15.00% |
| | Stepanate ® SCS, Stepan (INCI: Sodium Cumenesulphonate) | 1.00% |
| | Water | 5.00% |
| | REWOMID ® C 212, Evonik Industries (INCI: Cocamide MEA) | 1.50% |
| | TEGIN ® G 1100 Pellets, Evonik Industries, (INCI: Glycol Distearate) | 1.50% |
| C | TEXAPON ® NSO, Cognis, 28% strength (INCI: Sodium Laureth Sulphate) | 15.00% |
| | TEGO ® Alkanol 16, Evonik Industries (INCI: Cetyl Alcohol) | 0.50% |
| | Synthesis Example S6 | 1.50% |
| | Dimethicone (10000 mPa · s) | 1.50% |
| | Stepanate ® SCS, Stepan (INCI: Sodium Cumenesulphonate) | 1.00% |
| | Keltrol ®, CP Telco (INCI: Xanthan Gum) | 0.75% |
| | Preservative | q.s. |

Formulation Example 35

Conditioning Antidandruff Shampoo

| | | |
|---|---|---|
| A | TEGIN ® G 1100 Pellets, Evonik Industries (INCI: Glycol Distearate) | 3.00% |
| | TEXAPON ® NSO, Cognis, 28% strength (INCI: Sodium Laureth Sulphate) | 40.00% |
| B | Perfume | 0.30% |
| | Zinc-Pyrion NF, WeylChem, 48% strength (INCI: Zinc Pyrithione) | 2.00% |
| | Synthesis Example S6 | 2.00% |
| C | Water | 35.70% |
| | TEGO ® Carbomer 341 ER, Evonik Industries (INCI: Acrylates/C10-30 Alkyl Acrylate Crosspolymer) | 0.20% |
| | Water | 0.30% |
| | NaOH, 25% strength | 0.30% |
| D | REWOTERIC ® AM B U 185, Evonik Industries, 30% strength (INCI: Undecylenamidopropyl Betaine) | 12.50% |
| | ANTIL ® SPA 80, Evonik Industries (INCI: Isostearamide MIPA; Glyceryl Laurate) | 3.70% |
| E | Preservative | q.s. |

Formulation Example 36

Hair Colorant

| | |
|---|---|
| Water demineralized | 57.40% |
| TEGO ® Alkanol 1618, Evonik Industries, (INCI: Cetearyl Alcohol) | 12.00% |
| Eutanol ® G, BASF (INCI: Octyldodecanol) | 3.00% |
| REWOMID ® C 212, Evonik Industries (INCI: Cocamide MEA) | 1.50% |
| Super Hartolan ® B, Crodo (INCI: Lanolin Alcohol) | 3.00% |
| Avocado oil, Henry Lamotte (INCI: Persea Gratissima Oil) | 1.50% |
| Pristerene ® 4960, Uniquema (INCI: Stearic Acid) | 6.00% |
| EDTA BD, BASF (INCI: Disodium EDTA) | 0.10% |
| Texapon ® K12G, BASF (INCI: Sodium Lauryl Sulphate) | 0.50% |
| Propylene glycol | 5.00% |
| Timica Silver Sparkle, BASF (INCI: MICA; Titanium Dioxide) | 1.00% |
| Ammonia solution, 25% strength | 6.00% |
| 2,5-Diaminotoluenesulphonate, (INCI: Toluene-2,5-Diamine) | 1.40% |
| Rodol ® RS, Jos. H. Lowenstein & Sons (INCI: Resorcinol) | 0.30% |
| HC Blue A42, (INCI: 2,4-Diaminophenoxyethanol di HCl) | 0.10% |
| Sodium sulphite | 0.50% |
| Perfume | 0.20% |
| Synthesis Example S8 | 0.50% |

Formulation Example 37

Hair Colorant

| | |
|---|---|
| Water demineralized | 64.00% |
| TEGO ® Alkanol 1618, Evonik Industries (INCI: Cetearyl Alcohol) | 12.00% |
| Super Hartolan ® B, Croda (INCI: Lanolin Alcohol) | 2.50% |
| Meadowfoam ® Seed Oil, Fanning (INCI: Limnanthes Alba) | 1.00% |
| Pristerene ® 4960, Uniquema (INCI: Stearic Acid) | 5.50% |
| EDTA BD, BASF (INCI: Disodium EDTA) | 0.10% |
| Glycerin | 5.00% |
| Texapon ® N 70, BASF (INCI: Sodium Laureth Sulphate) | 2.00% |
| Monoethanolamine | 4.00% |
| 2,5-Diaminotoluene sulphonate, (INCI: Toluene-2,5-Diamine) | 0.90% |
| Rodol ® RS, Jos. H. Lowenstein & Sons (INCI: Resorcinol) | 0.20% |
| Jarocol ® 4A3MP, Vivimed Labs (INCI: 4-Amino-M-Cresol) | 0.60% |
| Rodol ® PAOC, Jos. H. Lowenstein & Sons (INCI: 4-Amino-2-Hydroxytoluene) | 0.50% |
| Uantox ® EBATE, Universal Preserv-A-Chem (INCI: Erythorbic Acid) | 0.50% |
| Perfume | 0.20% |
| Synthesis Example S6 | 1.00% |

Formulation Example 38

Hair Colorant

| | |
|---|---|
| Water demineralized | 67.50% |
| TEGO ® Alkanol 1618, Evonik Industries (INCI: Cetearyl Alcohol) | 10.00% |
| Eutanol ® G, BASF Cognis (INCI: Octyldodecanol) | 1.00% |
| REWOMID ® C 212, Evonik Industries (INCI: Cocamide MEA) | 2.00% |
| TEGIN ® VS, Evonik Industries (INCI: Glyceryl Stearate SE) | 5.00% |
| Fitoderm ®, Hispano Quimica S. A. (INCI: Squalane) | 1.00% |
| Coenzyme Q 10 | 0.10% |
| EDTA BD, BASF (INCI: Disodium EDTA) | 0.10% |
| Texapon ® K12G, BASF (INCI: Sodium Lauryl Sulphate) | 0.10% |
| Propylene glycol | 5.00% |
| Ammonia solution, 25% strength | 3.00% |
| Rodol ® ERN, Jos. H. Lowenstein & Sons (INCI: 1-Naphthol) | 0.30% |
| Imexine ® OAG, Chimex (INCI: 2-Methyl-5-Hydroxyethylaminophenol) | 1.00% |
| Colorex ® WP5, Teluca (INCI: 1-Hydroxyethyl 4,5-Diamino Pyrazole Sulphate) | 2.60% |
| Ascorbic acid | 0.30% |
| Perfume | 0.30% |
| Synthesis Example S8 | 0.70% |

Formulation Example 39

Hair Colorant

| | |
|---|---|
| Water demineralized | 60.70% |
| TEGO ® Alkanol 1618, Evonik Industries (INCI: Cetearyl Alcohol) | 13.00% |
| REWOMID ® C 212, Evonik Industries (INCI: Cocamide MEA) | 2.00% |
| Super Hartolan ® B, Croda (INCI: Lanolin Alcohol) | 2.50% |
| Avocado oil, Henry Lamotte (INCI: Persea Gratissima Oil) | 2.00% |
| Pristerene ® 4960, Uniquema (INCI: Stearic Acid) | 6.00% |
| EDTA BD, BASF (INCI: Disodium EDTA) | 0.10% |
| Texapon ® K12G, BASF (INCI: Sodium Lauryl Sulphate) | 0.10% |
| Propylene glycol | 5.00% |
| Ammonia solution, 25% strength | 6.00% |
| 2,5-Diaminotoluene sulphonate, (INCI: Toluene-2,5-Diamine) | 1.30% |
| Rodol ® RS, Jos. H. Lowenstein & Sons (INCI: Resorcinol) | 0.30% |
| Covastyle ® TBQ, LCW Les colorants Wackherr S. A. (INCI: t-Butyl Hydroquinone) | 0.30% |
| Perfume | 0.20% |
| Synthesis Example S6 | 0.50% |

Formulation Example 40

Shampoo

| | |
|---|---|
| TEXAPON ® NSO, Cognis, 28% strength (INCI: Sodium Laureth Sulphate) | 28.00% |
| REWOTERIC ® AM 2 C NM, Evonik Industries, 39% strength (INCI: Disodium Cocoamphodiacetate) | 4.00% |
| TEGO ® Betain F 50, Evonik Industries, 38% strength (INCI: Cocamidopropyl Betaine) | 7.00% |
| REWOMID ® C 212, Evonik Industries (INCI: Cocamide MEA) | 0.80% |
| ANTIL ® 171, Evonik Industries (INCI: PEG-18 Glyceryl Oleate/Cocoate) | 0.50% |
| N-Hance ® SP-100, Hercules (INCI: Acrylamidopropyl Trimonium Chloride/Acrylamide Copolymer) | |
| Polymer JR 400, Amerchol (INCI: Polyquatemium-10) | 0.10% |
| Jaguar C-162, Rhodia (INCI: Hydroxypropyl Guar Hydroxypropyltrimonium Chloride) | 0.20% |
| DC 193, Dow Corning (INCI: PEG-12 Dimethicone) | 0.40% |
| Synthesis Example S8 | 0.70% |
| Synthesis Example S5 | 0.60% |
| TEGIN ® D 1102, Evonik Industries (INCI: PEG-3 Distearate) | 0.40% |
| TAGAT ® CH 40, Evonik Industries (INCI: PEG-40 Hydrogenated Castor Oil) | 0.20% |
| Water | 56.00% |
| NaCl | 0.70% |
| Citric Acid | ad pH = ~5.5 |
| Perfume | q.s. |
| Preservative | q.s. |

While the present application has been particularly shown and described with respect to various embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims

What is claimed is:

1. A process for preparing an amino acid-modified siloxane, comprising:
reacting a salt of the general formula K+A− with at least one siloxane having at least one epoxy group and/or carbonate group, where
K+ is the organic cation cetyltrimethylammonium, and
A− is selected from the group consisting of arginate, lysinate, and histidate.

2. The process according to claim 1, wherein the at least one siloxane is a compound of general formula IV $$M_{a1}M^A_{a2}M^B_{a3}D_{b1}D^A_{b2}D^B_{b3}T_{c1}T^A_{c2}T^B_{c3}Q_{d1} \qquad \text{general formula IV}$$

with
$M=[R^{16}_3SiO_{1/2}]$
$M^A=[R^{17}R^{16}_2SiO_{1/2}]$
$M^B=[R^{18}R^{16}_2SiO_{1/2}]$
$D=[R^{16}_2SiO_{2/2}]$
$D^A=[R^{17}_1R^{16}_1SiO_{2/2}]$
$D^B=[R^{18}_1R^{16}_1SiO_{2/2}]$
$T=[R^{16}SiO_{3/2}]$
$T^A=[R^{17}SiO_{3/2}]$
$T^B=[R^{18}SiO_{3/2}]$
$Q=[SiO_{4/2}]$,
where
$R^{16}$ independently at each occurrence is identical or different, linear or branched, saturated or unsaturated hydrocarbon radicals having 1 to 30 carbon atoms or aromatic hydrocarbon radicals having 6 to 30 carbon atoms,
$R^{17}$ independently at each occurrence is identical or different radicals containing epoxy and/or carbonate groups,
$R^{18}$ independently at each occurrence is identical or different, linear or branched, saturated or olefinically unsaturated hydrocarbon radicals having 8 to 30 carbon atoms,
an aromatic hydrocarbon radical with 6 to 40 carbon atoms, an alkylaryl radical with 7 to 40 carbon atoms,
a linear or branched, optionally double bond-containing aliphatic hydrocarbon radical with 2 to 30 carbon atoms interrupted by one or more heteroatoms,
a linear or branched, optionally double bond-containing aliphatic hydrocarbon radical having from 2 to 30 carbon atoms, which is interrupted by one or more functionalities selected from the group of —O—C(O)—, —(O)C—O—, —NH—C(O)—, —(O)C—NH, —(CH$_3$)N—C(O)—, —(O)C—N(CH$_3$)—, —S(O$_2$)—O—, —O—S(O$_2$)—, —S(O$_2$)—NH—, —NH—S(O$_2$)—, —S(O$_2$)—N(CH$_3$)—, and —N(CH$_3$)—S(O$_2$)—,
a terminally OH, OR', NH$_2$, N(H)R', N(R')$_2$ functionalized linear or branched optionally double bond-containing aliphatic or cycloaliphatic hydrocarbon radical with 1 to 30 carbon atoms, wherein R' is an optionally double bond-containing C1 to C30 alkyl radical, or
a blockwise or randomly constructed polyether according to —(R$^5$—O)$_n$—R$^6$, where R$^5$ is a linear or branched hydrocarbon radical containing 2 to 4 carbon atoms, n is 1 to 100, and R$^6$ is hydrogen, a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, or a radical —C(O)—$R^7$, where $R^7$ is a linear or branched optionally double bond-containing aliphatic hydrocarbon radical with 1 to 30 carbon atoms, an optionally double bond-containing cycloaliphatic hydrocarbon radical with 5 to 40 carbon atoms, an aromatic hydrocarbon radical with 6 to 40 carbon atoms, an alkylaryl radical with 7 to 40 carbon atoms, a1=0 to 200,
a2=0 to 30,
a3=0 to 30,
b1=3 to 5000,
b2=0 to 100,
b3=0 to 100,
c1=0 to 30,
c2=0 to 30,
c3=0 to 30,
d1=0 to 30,
with the proviso that at least one of the indices a2, b2 or c2≠0.

3. The process of claim 1 further comprising:
reacting the amino acid-modified siloxane with a further organic component containing epoxy groups.

4. The process of claim 1 further comprising purifying the amino acid-modified siloxane.

* * * * *